(12) United States Patent
Lee et al.

(10) Patent No.: US 8,217,012 B2
(45) Date of Patent: Jul. 10, 2012

(54) PEPTIDES FOR TARGETING APOPTOTIC CELLS AND USES THEREOF

(75) Inventors: Byung Heon Lee, Daegu (KR); In San Kim, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 265 days.

(21) Appl. No.: 12/465,007

(22) Filed: May 13, 2009

(65) Prior Publication Data

US 2009/0285754 A1  Nov. 19, 2009

(30) Foreign Application Priority Data

May 14, 2008  (KR) ........................ 10-2008-0044410

(51) Int. Cl.
- *A61K 38/08* (2006.01)
- *A61K 49/00* (2006.01)
- *A61K 51/00* (2006.01)
- *C07K 7/06* (2006.01)

(52) U.S. Cl. .................... 514/21.8; 514/13.3; 514/19.2; 424/9.1; 530/329

(58) Field of Classification Search .................. None
See application file for complete search history.

(56) References Cited

U.S. PATENT DOCUMENTS

| 5,595,756 A * | 1/1997 | Bally et al. ..................... 424/450 |
| 2008/0014583 A1 * | 1/2008 | Montminy et al. ............... 435/6 |

OTHER PUBLICATIONS

Sporn MB, Suh N, "Chemoprevention of cancer," Carcinogenesis, 2000, 21:(3): 525-530.*
Auerbach R, Akhtar N, Lewis RL, Shinners BL, "Angiogenesis assays: Problems and pitfalls," Cancer and Metastasis Reviews, 2000, 19: 167-172.*
Gura Trisha, "Systems for Identifying New Drugs Are Often Faulty," Science, 1997, 278: 1041-1042.*
Jain RK, "Barriers to Drug Delivery in Solid Tumors," Scientific American, 1994, 58-65.*
Neidle, Stephen, "Cancer Drug Design and Discovery," Elsevier/Academic Press, 2008:427-431.*
Stroke from Merck manual from http://www.merckmanual.com/professional/sec17/ch221a.html, pp. 1-4. Accessed Aug. 12, 2011.*
Arteriosclerosis from Merck manual from http://www.merckmanual.com/professional/sec07/ch077b.html, pp. 1-5. Accessed Aug. 12, 2011.*

* cited by examiner

*Primary Examiner* — Julie Ha
(74) *Attorney, Agent, or Firm* — Edwards Wildman Palmer LLP

(57) ABSTRACT

A peptide capable of specifically targeting apoptotic cells undergoing apoptosis and a use thereof is described. Peptides having an amino acid sequence represented by any one of SEQ ID NO: 1 to SEQ ID NO: 12 targeted apoptotic cell. Uses for compositions comprising the peptides include detection of apoptotic cells drug delivery and imaging. The peptide of the present invention effectively detects apoptosis which is involved in tissues of neoplastic disease, myocardial infarction, stroke and arteriosclerosis. Accordingly, the peptide of the present invention may be bound to an imaging or treatment reagent to be used in diagnosis of diseases, imaging of drug reactions, and treatment for diseases by selective drug delivery.

17 Claims, 10 Drawing Sheets

(9 of 10 Drawing Sheet(s) Filed in Color)

FIG. 9
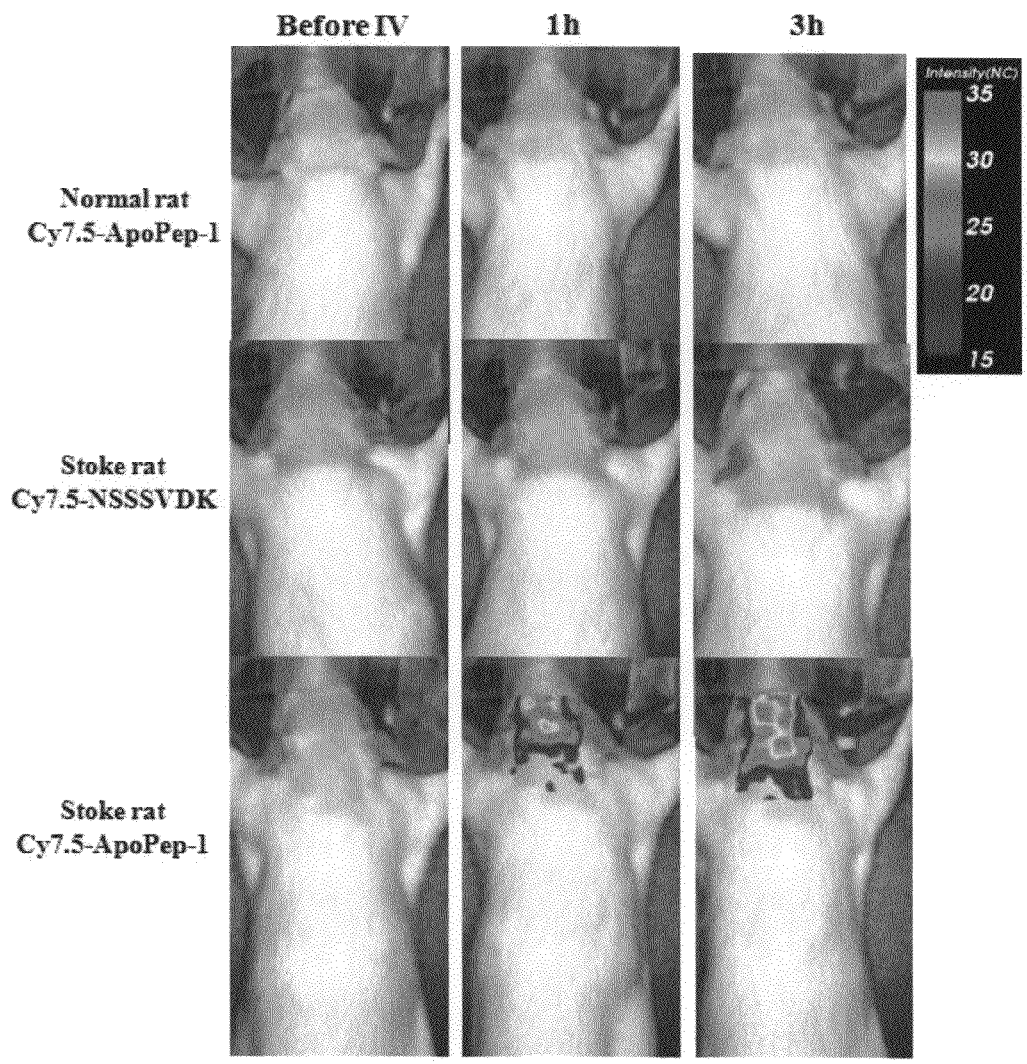
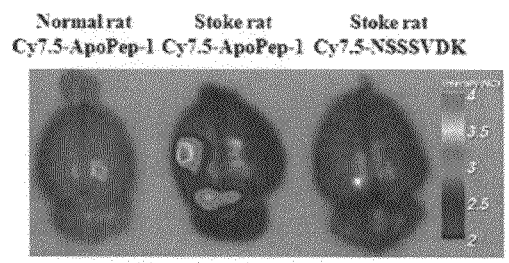

PEPTIDES FOR TARGETING APOPTOTIC CELLS AND USES THEREOF

CROSS-REFERENCE TO RELATED APPLICATION

This application claims under 35 U.S.C. §119(a) the benefit of Korean Patent Application No. 10-2008-0044410 filed May 14, 2008, the entire contents of which are incorporated herein by reference.

TECHNICAL FIELD

This application claims priority to Korean Patent Application No. 10-2008-0044410 filed on May 14, 2008, which is hereby incorporated by reference herein.

The present invention relates to peptides capable of specifically targeting apoptotic cells undergoing apoptosis and a use thereof. More particularly, it relates to peptides having an amino acid sequence represented by anyone selected from the group consisting of SEQ ID NO: 1 to SEQ ID NO: 12 and targeting apoptotic cells, a composition for detection of apoptotic cells comprising the same as an effective ingredient, a composition for drug delivery comprising the same as an effective ingredient, a composition for imaging comprising the same as an effective ingredient, and so on.

RELATED ART

Apoptosis is the process of programmed cell death resulting in the death of unnecessary or harmful cells during an organism's life cycle. In Greek, apoptosis means "to fall". It was named so by comparing the process of cell death to the falling of petals from a flower, and was first observed in 1972 by Kerr et al. (Kerr et al., *Br. J. Cancer,* 1972, 26:239-257). Apoptosis plays an important role in physiological events, including cell development, differentiation, immunity and the like (Meier et al., *Nature,* 2000, 407:796-801). Apoptosis is also important in several pathological conditions and diseases. For example, successful treatment with anticancer drugs involves apoptosis in the tumor tissue (Thomson, *Science,* 1995, 267:1456-1462). In contrast, decreased apoptosis results in formation of tumors. As another example, apoptosis of brain cells or myocardial cells occurs during stroke or myocardial infarction due to the shortage of blood supply to the brain or heart (Du et al, *J. Cereb. Blood Flow Metab.,* 1996, 16:195-201; Narula et al., *New Engl. J. Med.,* 1996, 335:1182-1189). In addition, apoptosis occurs frequently in organ transplant rejection or such diseases as autoimmune disease, degenerative cerebral nerve disorder, arteriosclerosis and viral infection (Thomson, *Science,* 1995, 267:1456-1462; Kageyama et al., *Ann. Thorac. Surg.,* 1998, 65:1604-1609).

Apoptosis is very important in clinical diagnosis and treatment. Therefore, imaging of apoptosis may be of great help to early diagnosis of degenerative cerebral nerve disorders (Alzheimer's disease, Parkinson's disease, etc.), monitoring of disease progression in myocardial infarction and stroke, monitoring of cancer therapeutic effect following anticancer drug treatment, decision of the possibility of rupture of atheromatous plaque, or the like, related with excessively increased apoptosis. Further, a selective delivery of a therapeutic or protecting agent to apoptotic cells may significantly improve therapeutic effect while reducing side effects.

One of the early events occurring in apoptotic cells is the change of the distribution of phospholipids that constitute the cell membrane. The most characteristic among them is the exposure of phosphatidylserine to outside of the cell membrane. Usually, phosphatidylserine is kept inside the cell membrane, but, when a cell receives an apoptotic signal or when a red blood cell ages, it is exposed to outside of the cell membrane (Fadeel, B. et al., *Cell Mol. Life. Sci.,* 2003, 60:2575-2585). A macrophage recognizes the exposed phosphatidylserine through a receptor on the cell surface and phagocytoses the apoptotic cell (Fadok, V. A. et al., *J. Immunol.* 1992, 148:2207-2216; Fadok, V. A. et al., *Nature* 2000, 405:85-90; Park, S. Y. et. al., *Cell Death Differ.,* 2008, 15:192-201). A large number of tumor cells show increased expression of phosphatidylserine outside the cell membrane (Utsugi, T. et al., *Cancer Res.* 1991, 15:3062-3066; Ran, S. et al., *Cancer Res.* 2002, 62:6132-6140; Woehlecke, H. et al., *Biochem. J.* 2003, 376:489-495). Further, the vascular endothelial cells in a tumor tissue expose phosphatidylserine outside of the cell membrane (Ran, S. et al., *Cancer Res.* 2002, 62:6132-6140; Zwaal, R. F. A. et al., *Blood.* 1997, 89:1121-1132). Therefore, in various situations especially including tumors, phosphatidylserine is deemed as a target material for diagnosis, treatment and treatment monitoring.

At present, the protein annexin V is generally used to detect phosphatidylserine on the surface of apoptotic cells. It is a 36 kDa protein and binds to phosphatidylserine with strong affinity (Vermes, I. et al., *Immunol. Methods.* 1995, 184:39-51). Although annexin V is a very useful targeting material or probe for in vitro application, its in vivo application is reported to be restricted because of, for example, slow removal out of the body due to large molecular weight (Vermeersch, H., et al., *Nucl. Med. Commun.* 2004, 25:259-263; Belhocine, T. Z. et al., *J. Proteome Res.* 2004, 3:345-349).

SUMMARY

The inventors of the present invention have worked to develop new proteins or fragments thereof capable of specifically and early targeting apoptotic cells in vivo. As a result, we have verified that a peptide having an amino acid sequence represented by anyone selected from the group consisting of SEQ ID NO: 1 to SEQ ID NO: 12 is capable of specifically targeting apoptotic cells, and completed the present invention.

Accordingly, an object of the present invention is to provide a peptide specifically targeting apoptotic cells and a use thereof.

To attain the object, in an aspect, the present invention provides a peptide having an amino acid sequence represented by anyone selected from the group consisting of SEQ ID NO: 1 to SEQ ID NO: 12 and specifically targeting apoptotic cells.

In another aspect, the present invention provides a polynucleotide encoding the peptide.

In another aspect, the present invention provides a composition for detection of apoptotic cells comprising the peptide as an effective ingredient.

In another aspect, the present invention provides a composition for drug delivery comprising the peptide as an effective ingredient.

In another aspect, the present invention provides a pharmaceutical composition for prevention and treatment of neoplastic disease comprising the peptide and an antitumor agent bound thereto as effective ingredients.

In another aspect, the present invention provides a composition for imaging neoplastic disease site comprising the peptide as an effective ingredient.

In another aspect, the present invention provides a pharmaceutical composition for treatment of stroke comprising the peptide and a nerve cell protecting agent bound thereto as effective ingredients.

In another aspect, the present invention provides a composition for imaging stroke site comprising the peptide as an effective ingredient.

In another aspect, the present invention provides a pharmaceutical composition for treatment of myocardial infarction comprising the peptide and a myocardial cell protecting agent bound thereto as effective ingredients.

In another aspect, the present invention provides a composition for imaging myocardial infarction site comprising the peptide as an effective ingredient.

In another aspect, the present invention provides a pharmaceutical composition for treatment of arteriosclerosis comprising the peptide and an anti-arteriosclerosis agent bound thereto as effective ingredients.

In another aspect, the present invention provides a composition for imaging arteriosclerosis site comprising the peptide as an effective ingredient.

In another aspect, the present invention provides a use of the peptide for detection of apoptotic cells.

In another aspect, the present invention provides a use of the peptide for drug delivery.

In another aspect, the present invention provides a method for drug delivery comprising administering the peptide and a drug bound thereto to a subject in need thereof at an effective dose.

In another aspect, the present invention provides a use of the peptide and an antitumor agent bound thereto for the preparation of an agent treating neoplastic disease.

In another aspect, the present invention provides a method for treatment of neoplastic disease comprising administering the peptide and an antitumor agent bound thereto to a subject in need thereof at an effective dose.

In another aspect, the present invention provides a use of the peptide and an antistroke agent bound thereto for the preparation of an agent treating stroke.

In another aspect, the present invention provides a method for treatment of stroke comprising administering the peptide and an antistroke agent bound thereto to a subject in need thereof at an effective dose.

In another aspect, the present invention provides a use of the peptide and an anti-myocardial infarction agent bound thereto for the preparation of an agent treating myocardial infarction.

In another aspect, the present invention provides a method for treatment of myocardial infarction comprising administering the peptide and an anti-myocardial infarction agent bound thereto to a subject in need thereof at an effective dose.

In another aspect, the present invention provides a use of the peptide and an anti-arteriosclerosis agent bound thereto for the preparation of an agent treating arteriosclerosis.

In another aspect, the present invention provides a method for treatment of arteriosclerosis comprising administering the peptide and an anti-arteriosclerosis agent bound thereto to a subject in need thereof at an effective dose.

In another aspect, the present invention provides a use the peptide for imaging a disease site selected from a group consisting of neoplastic disease, stroke, myocardial infarction and arteriosclerosis.

In another aspect, the present invention provides a method for imaging a disease site selected from a group consisting of neoplastic disease, stroke, myocardial infarction and arteriosclerosis comprising administering the peptide to a subject in need thereof at an effective dose.

BRIEF DESCRIPTION OF THE DRAWINGS

The patent or application file contains at least one drawing executed in color. Copies of this patent or patent application publication with color drawing(s) will be provided by the Office upon request and payment of necessary fee.

FIG. 9 shows the images obtained as follows. To a stroke rat model, which was subjected to 2 hours of middle cerebral artery occlusion followed by reperfusion, and a normal rat, the peptide having an amino sequence represented by SEQ ID NO: 1 (ApoPep-1), which was labeled with Cy7.5 NIR fluorescence, was intravenously injected. One and three hours later, NIR images of the head portion were obtained (A). Then, NIR images of the brains of the rats of the 3 hour group were obtained (B) (ApoPep-1-Cy7.5: Cy7.5-labeled ApoPep-1; NSSSVDK-Cy7.5: Cy7.5-labeled control peptide).

DETAILED DESCRIPTION

Figure 1:
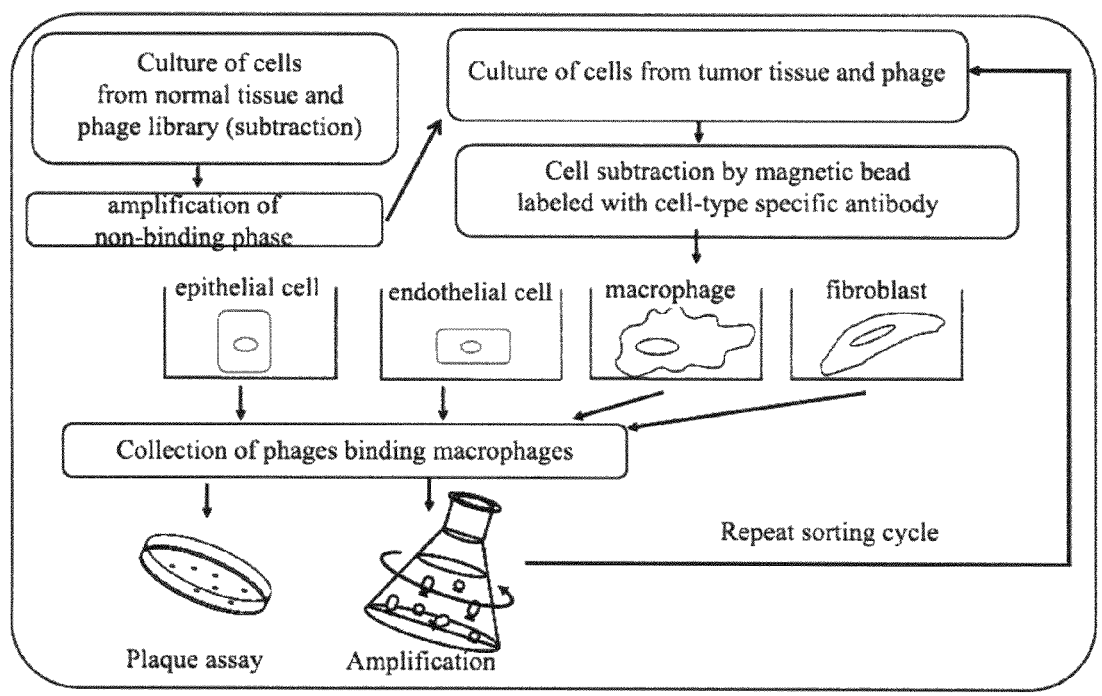
FIG. 1 schematically illustrates a process of screening phages specifically binding to various cells (tumor cells, endothelial cells, macrophages and fibroblasts) derived from human primary lung cancer tissue.

Hereinafter, the present invention will be described in further detail.

Based on the finding that a polypeptide having an amino acid sequence represented by anyone selected from the group consisting of SEQ ID NO: 1 to SEQ ID NO: 12 specifically binds to apoptotic cells undergoing apoptosis, the present invention provides a polypeptide with a novel sequence having an amino acid sequence represented by anyone selected from the group consisting of SEQ ID NO: 1 to SEQ ID NO: 12, a composition for detection of apoptotic cells comprising the polypeptide and so on, as a use thereof.

The peptide of the present invention is a peptide which specifically binds to apoptotic cells undergoing apoptosis and has an amino acid sequence represented by anyone selected from the group consisting of SEQ ID NO: 1 to SEQ ID NO: 12. As used herein, a peptide fragment refers to any peptide, protein, mimetic peptide, compound and biological agent capable of specifically binding to apoptotic cells. The peptide of the present invention may be derived from the nature or may be synthesized by a known peptide synthesis technique.

The peptide of the present invention may comprise the peptide having naturally occurring amino acid sequences and variants having modified sequences as well. The variants of the peptide of the present invention refer to peptides having different sequences from the amino acid sequence selected from the group consisting of SEQ ID NO:1 to SEQ ID NO:12, prepared by deletion, insertion, non-conserved or conserved substitution, substitution of amino acid analog or their combinations. The silent alteration of amino acid residues not to substantially impair protein activity is well known to one skilled in the art (H. Neurath, R. L. Hill, The Proteins, Academic Press, New York, 1979).

In addition, the peptide of the present invention may comprise modifications such as phosphorylation, sulfation, acrylation, glycosylation, methylation, farnesylation and the like.

Further, the present invention provides a polynucleotide having a base sequence encoding the peptide of the present invention. The polynucleotide may be any combination of base sequences, which, consequently, is capable of encoding the peptide of the present invention.

In addition, the present invention provides a vector having a base sequence encoding the peptide of the present invention and a transformant transformed by the vector.

The vectors of the present invention include a plasmid vector, a cosmid vector, a bacteriophage vector and a viral vector, but are not limited thereto. The vectors of the present invention may conventional cloning vectors or expression vectors, and the expression vectors comprise regulatory elements for gene expression such as a promoter, operator, an initiation codon, a stop codon, a polyadenylation signal, and an enhancer(promoting gene), and a variety of vectors can be prepared according to the purpose. Furthermore, the said vectors may comprise selective markers for selecting host cells comprising the vector and in case of replicable vectors, they comprise replication origin.

The transformation with the said vector can be carried out according to any known transformation method in the pertinent art. Preferably, microprojectile bombardment, electroporation, $CaPO_4$ precipitation, $CaCl_2$ precipitation, PEG-mediated fusion, microinjection and liposome-mediated method, but not limited to. The transformant may be Escherichia coli, Bacillus subtilis, Streptomyces, Pseudomonas, Proteus mirabilis and Staphylococcus, Agrobacterium tumefaciens, but not limited to.

Through various experiments aimed at verifying the functions of peptides identified to specifically bind to apoptotic cells, the inventors of the present invention have confirmed that the peptide of the present invention specifically recognizes cultured tumor cells, normal epithelial cells and macrophages undergoing apoptosis and binds to the cells. Further, we have verified that the peptides of the present invention are capable of targeting apoptotic cells in a tumor tissue and, thereby, enabling in vivo imaging and monitoring thereof. Accordingly, it was confirmed that the peptide of the present invention may be utilized for a composition for detection of apoptotic cells, for a composition for diagnosis or monitoring of apoptosis in tumor tissue, and for a pharmaceutical composition for prevention and treatment of neoplastic disease along with an antitumor agent.

More specifically, in an example of the present invention, phages specifically binding to macrophages or endothelial cells separated from a tumor tissue were screened using a commercially available T7 phage library. Through a total of 3 rounds of screening, phages capable of specifically binding to the cells were screened. Through sequencing, it was confirmed that peptides having the amino acid sequence CQRPPR (SEQ ID NO: 1), CSVAPR (SEQ ID NO: 2), CNRPPR (SEQ ID NO: 3), CQKPPR (SEQ ID NO: 4), CQRPPK (SEQ ID NO: 5), CNKPPR (SEQ ID NO: 6), CNRPPK (SEQ ID NO: 7), CQKPPK (SEQ ID NO: 8), CNKPPK (SEQ ID NO: 9), CTVAPR (SEQ ID NO: 10), CSVAPK (SEQ ID NO: 11) and CTVAPK (SEQ ID NO: 12) were mainly screened out. It seems that the peptides of the present invention are synthesized by the nucleotides inserted with termination codon after 5th amino acid in the phage library of the present invention randomly encoding $CX_7C$ peptide.

In another example of the present invention, it was investigated whether the peptide of the present invention targets a tumor xenotransplanted under the skin of nude mouse and which cell it binds to. As a result, the peptides of the present invention were confirmed, when injected into blood, to target the tumor tissue and mainly bind to the tumor cells undergoing apoptosis rather than macrophages or endothelial cells, from tissue staining.

In another example of the present invention, the binding specificity of the screened peptides to the apoptotic cells induced by chemical was investigated. As a result, the peptide strongly bound to the apoptotic cells treated with an apoptosis-inducing agent, whereas it hardly bound to the untreated cells. Further, the binding of the peptide to the apoptotic cells was not inhibited by the prior treatment of annexin V at high concentration. In addition, the peptide was confirmed to recognize and bind to the cells in the later stage of apoptosis as well as the early stage.

In another example of the present invention, it was investigated whether the peptide of the present invention targets a tumor xenotransplanted under the skin of nude mouse and whether it can be imaged. As a result, the peptide of the present invention targeted the tumor tissue in the group to which the peptide of the present invention was injected into blood following doxorubicin treatment and the targeting could be imaged by fluorescent label. In contrast, the targeting was not observed in the group to which the peptide of the present invention was injected without the drug treatment as well as in the group to which a control peptide was injected following the drug treatment.

In another example of the present invention, it was investigated whether the peptide of the present invention labeled with a radioactive isotope targets a tumor xenotransplanted under the skin of nude mouse and whether it can be imaged by positron emission tomography (PET). As a result, the targeting of the peptide of the present invention was confirmed in the group to which the peptide of the present invention labeled with $^{123}$I(I-123) was injected into blood following doxorubicin treatment, through increased PET image signals at the tumor site. In contrast, in the group to which $^{18}$F(F-18)-labeled fluorodeoxyglucose (FDG), which is frequently used for PET, was injected, the PET image signals decreased at the tumor site following the drug treatment.

In another example of the present invention, it was investigated whether the peptide of the present invention targets in the aorta of an arteriosclerosis-induced mouse and whether it can be imaged. As a result, the peptide of the present invention targeted in the aorta of arteriosclerotic mice in the group to which the peptide of the present invention was injected into blood, and the targeting could be imaged using a fluorescent label. In contrast, the targeting of the peptide could not be observed in the group of arteriosclerotic mice to which a control peptide was injected or in the group of normal mice.

In another example of the present invention, it was investigated whether the peptide of the present invention targets in the brain tissue of a stroke-induced rat and whether it can be imaged. As a result, the peptide of the present invention targeted in the damaged brain tissue of the group of stroke-induced rats to which the peptide of the present invention was injected into blood, and the targeting could be imaged using a fluorescent label. In contrast, the targeting of the peptide could not be observed in the group of stroke-induced rats to which a control peptide was injected or in the group of normal rats.

In another example of the present invention, it was investigated whether the peptide of the present invention targets in the cardiac tissue of a myocardial infarction-induced rat and whether it can be imaged. As a result, the peptide of the present invention targeted in the damaged cardiac tissue of the group of myocardial ischemia-induced rats to which the peptide of the present invention was injected into blood, and the targeting could be imaged using a fluorescent label. In contrast, the targeting of the peptide could not be observed in the group of myocardial ischemia-induced rats to which a control peptide was injected or in the group of normal rats.

To conclude, it was confirmed that the peptide of the present invention binds specifically to apoptotic cells, thereby recognizing apoptosis and targeting tumors in vivo.

The following references may be referred to the processes for the said nucleotides and proteins (Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990)).

Accordingly, the present invention provides an composition for detecting apoptotic cells comprising an peptide having an amino acid sequences represented by anyone selected from the group consisting of SEQ ID NO: 1 to SEQ ID NO: 12 of the present invention as an effective ingredient.

For easy identification, detection and qualification of binding the peptide of the present invention with apoptotic cell, the peptide of the present invention may be provided as a form of labeled. The said detectable label material may be coloring enzyme (for example, peroxidase, alkaline phosphatase), radioactive isotope(for example, $^{18}$F, $^{124}$I, $^{125}$I, $^{32}$P, $^{35}$S), chromophore, scintillating materials or fluorescent materials (for example: FITC, RITC, fluorescent proteins(GFP (Green Fluorescent Protein); EGFP (Enhanced Green Fluorescent Protein), RFP (Red Fluorescent Protein); DsRed (Discosoma sp. red fluorescent protein); CFP (Cyan Fluorescent Protein), CGFP (Cyan Green Fluorescent Protein), YFP (Yellow Fluorescent Protein), Cy3, Cy5 and Cy7.5), super paramagnetic particles or ultrasuper paramagnetic particles.

Detection techniques based on labeling are well known in the art. Detections may be made, for example, as follows. In case a fluorescent material is used as a detectable label, immunofluorescence staining may be employed. For example, the peptide of the present invention labeled with a fluorescent material may be reacted with a sample, and, following the removal of unbound or unspecifically bound product, fluorescence emitted by the peptide may be observed under a fluorescence microscope. In case that an enzyme is used as a detectable label, absorbance may be measured following an enzymatic reaction with a substrate. And, in case that a radioactive material is used, a radioactive radiation may be measured. The detection result may be imaged using a known imaging technique.

The present invention further provides a method for detecting apoptotic cells comprising the steps of: (a) mixing the polypeptide of the present invention with a sample; (b) removing unbound or unspecifically bound polypeptide; and (c) detecting the binding of the polypeptide and the location thereof. The polypeptide of the present invention and the detection of the polypeptide of the present invention bound to apoptotic cells may be described above or carried out as described above or according to known methods.

Further, the present invention provides a use of the polypeptide of the present invention for detection of apoptotic cells. The polypeptide of the present invention and the detection of the polypeptide of the present invention bound to apoptotic cells may be described above or carried out as described above or according to known methods.

Since the peptide of the present invention is capable of specifically binding to apoptotic cells, it may be utilized as an intelligent drug carrier which selectively delivers a drug to the cells. Accordingly, the present invention provides a composition for drug delivery comprising the peptide of the present invention as an effective ingredient. Further, the present invention provides a use of the peptide of the present invention for drug delivery. In addition, the present invention provides a method for drug delivery comprising administering the peptide of the present invention and a drug bound thereto to a subject in need thereof at an effective dose.

As described above, apoptosis occurs not only in tumor cells, but also in the cells affected by stroke, myocardial infarction or arteriosclerosis (Thomson, *Science*, 1995, 67:1456-1462; Du et al, *J. Cereb. Blood Flow Metab.*, 1996, 16:195-201; Narula et al., *New Engl. J. Med.*, 1996, 335: 1182-1189). Accordingly, the composition for drug delivery may be specific to neoplastic disease, stroke, myocardial infarction or arteriosclerosis. As used herein, the neoplastic disease is a disease exhibiting pathological conditions due to malignant tumors. Examples of neoplastic disease may include, although not limited thereto, colon cancer, lung cancer, stomach cancer, esophageal cancer, pancreatic cancer, gallbladder cancer, renal cancer, bladder cancer, prostate cancer, testicular cancer, cervical cancer, endometrial cancer, choriocarcinoma, ovarian cancer, breast cancer, thyroid cancer, brain cancer, head and neck cancer, malignant melanoma, skin cancer, liver cancer, leukemia, lymphoma, multiple myeloma, chronic myelogenous leukemia, neuroblastoma and aplastic anemia.

When used in combination with existing antitumor agent, anti-myocardial infarction agent, antistroke agent or anti-arteriosclerosis agent, the peptide of the present invention may selectively deliver the agents to the disease site, i.e., tumor site, myocardial infarction site, stroke site or arteriosclerosis site. Hence, the drug efficiency may be improved and side effects on normal tissues may be significantly reduced.

The antitumor agent that can be used in combination with the peptide of the present invention may be anyone that is used for treatment of a tumor. For example, paclitaxel, doxorubicin, vincristine, daunorubicin, vinblastine, actinomycin-D, docetaxel, etoposide, teniposide, bisantrene, homoharringtonine, Gleevec (STI-571), cisplatin, 5-fluorouracil, adriamycin, methotrexate, busulfan, chlorambucil, cyclophosphamide, melphalan, nitrogen mustard, nitrosourea, etc. may be included. And, the anti-myocardial infarction agent, antistroke agent and anti-arteriosclerosis agent may be anyone used for the treatment of the diseases. For example, thrombolytic drugs such as streptokinase, urokinase, alteplase, etc, which are used for removal of thrombis blocked blood vessel in stroke and myocardial infarction, may be used. Further, myocardial cell protecting agents such as angiotensin II inhibitor, aldosterone receptor inhibitor, erythropoietin, etc. may be used. Also, brain nerve cell protecting agents such as N-methyl-D-aspartate (NMDA) receptor inhibitor may be used. Further, cholesterol synthesis inhibiting or blood cholesterol level reducing drugs such as lovastatin, vascular smooth muscle cell (VSMC) proliferating inhibiting drugs such as rapamycin, antiinflammatory drugs such as Celebrex, platelet coagulation inhibiting drugs such as Ticlopin, matrix metalloproteinase inhibiting drugs such as marimastat, Trocade, etc. may be used. The binding of the peptide of the present invention with the agents may be carried out by the methods known in the art, for example, by covalent bonding, crosslinking, or the like. For this, the peptide of the present invention may be chemically modified insofar as its activity is not lost, if necessary. The amount of the peptide of the present invention included in the composition of the present invention may be different depending on the kind and amount of the anticancer drug that the peptide binds to.

As used herein, the "effective amount" refers to the amount effective in treating the subject diseases, and the "subject" refers to mammals, particularlly, animals comprising human. The subject may be human in need of treatment.

Meanwhile, the present invention provides a pharmaceutical composition for prevention and treatment of neoplastic disease comprising the peptide of the present invention and an antitumor agent bound thereto as effective ingredients. In addition, the present invention provides a use of the peptide of the present invention and an antitumor agent bound thereto for the preparation of an agent treating neoplastic disease. Furthermore, the present invention provides a method for treatment of neoplastic disease comprising administering the peptide of the present invention and an antitumor agent bound thereto to a subject in need thereof at an effective dose.

At this time, in the said pharmaceutical composition, antitumor agent, binding method and neoplastic disease are the same as can be seen from the foregoing Meanwhile, a pharmaceutical composition of the present invention may be prepared by formulated into pure form or appropriate forms with pharmaceutically acceptable carriers. As used herein, the term "pharmaceutically acceptable" means nontoxic composition which is physiologically acceptable and, when administered to human beings, generally does not cause allergic reactions, such as gastrointestinal disorder and dizziness, or similar reactions thereto. The said carriers may comprise all kinds of solvents, dispersing medium, water-in-oil or oil-in-water emulsion, aquatic composition, liposome, microbead and microsome, biodegradable nanoparticles.

Meanwhile, the pharmaceutical composition of the present invention may be formulated with appropriate carriers according to administration routes. The pharmaceutical composition of the present may be administered orally or parenterally, but not limited thereto. The parenteral administration routes may comprise route by intracutaneous, intranasal, intraperitoneal, intramuscular, subdural, or intravenous and the like.

For oral administration, which is not limited thereto, the composition of the present invention can be formulated in the form of powder, granule, tablets, pills, sugar-coated tablets, capsules liquor, gel, syrup, suspension, wafer and the like. The appropriate carriers may comprise sugars comprising lactose, dextrose, sucrose, sorbitol, mannitol, xylitol, erythritol and maltitol, starches comprising corn starch, wheat starch, rice starch and potato starch, celluloses comprising cellulose, methylcellulose, sodium carboxymethylcellulose, and hydroxypropylmethyl- cellulose, and fillers such as gelatin and polyvinylpyrrolidone. In addition, it may comprise crosslinked polyvinylpyrrolidone, agar, alginic acid or a sodium salt thereof as a solutionizer. Furthermore, the said pharmaceutical composition may further comprise antiagglutination reagent, lubricant, humectant, flavor, emulsifying agent and antiseptic.

In addition, in case of parenteral administration, the pharmaceutical composition of the present invention could be formulated, as known in the art, in the form of injectable formulation, transdermal formulation and intranasal formulation with proper parenteral carriers. The injectable formulation must be sterilized and prevented from contamination of microorganisms such as fungi and bacteria. In case of injectable formulation, the carriers may comprise, but not limited to, water, ethanol, polyol (for example, glycerol, propylene glycol, liquid polyethylene glycol and the like), mixture of these and/or solvent including vegetable oils or dispersion medium. More preferably, the carriers may comprise Hank's solution, Ringer's solution, PBS(phosphate buffered saline) containing triethanolamine, or isotonic solutions such as water for injection, 10% ethanol, 40% propylene glycol, and 5% dextrose. To prevent from contamination of microorganisms, the injectable agents may comprise additionally anti-fungal reagents and anti-bacterial reagents such as parabens, chlorobutanol, phenol, sorbic acid, thimerosal. In addition, the injectable formulation may also comprise isotonic solution such as saccharides or sodium chloride in mose cases. These formulations are described in Remington's Pharmaceutical Science, 15th Edition, 1975, Mack Publishing Company, Easton, Pennsylvania which is well know prescription manual.

In case of intranasal preparations, the inventive pharmaceutical composition may comprise proper propellant such as dichlorofluoromethane, trichlorofluoromethane, dichlorotetafluoroethane, carbon dioxide, and the like. By these propellants, the composition could be released easily from pressurized pack or spray container in the form aerosol spray. In case of the pressurized aerosol, administration dosage may be set by placing a valve. For example, gelatin capsules and cartridges which are used in inhalers and insufflators may comprise a proper powder mixture such as a chemical compound, lactose, or starches Another carriers which is pharmaceutically acceptable is disclosed in Remington's Pharmaceutical Sciences, 19th ed. Mack Publishing Company, Easton, Pa., 1995.

The inventive pharmaceutical composition may further comprise one or more buffers (for example, saline or PBS), carbohydrates (for example, glucose, mannose, sucrose, or dextran), antioxidants, bacteriostats, chelating reagents (for example, EDTA or glutathione), adjuvant (for example, aluminium hydroxide), suspension reagent, concentrating reagent, and/or preservatives.

Also, the inventive pharmaceutical composition may be formulated by using the method which is known in the art, to provide rapid, continuous or delayed release after administered to a mammalian.

The pharmaceutical composition formulated by the said method may be administered by oral, transdermal, subcutaneous, intramuscular, or intravenous with effective amount. The said "effective amount" means the amount of compound or extract which makes traceable for diagnosis or treatment, when it is administered to a patient. The administration amount of the pharmaceutical composition of the present invention may be suitably determined by considering administration route, administration subject, the subject disease and severity thereof, age, sex, body weight, variation of the individuals, and health condition. The pharmaceutical composition of the present invention containing the inventive polypeptide may vary depending on the severity of the disease, but the effective ingredient may be generally administered at an effective dose of 10 μg-10 mg several times daily.

Further, since the peptide of the present invention specifically binds to apoptotic cells, it may be useful for imaging and diagnosis of neoplastic disease site. Accordingly, the present invention provides a composition for imaging and diagnosis of neoplastic disease comprising the peptide as an effective ingredient. The present invention further provides a use of the peptide of the present invention for imaging neoplastic disease site. In addition, the present invention provides a method for imaging neoplastic disease site comprising administrating the peptide of the present invention to a subject in need thereof at an effective dose. The imaging and diagnosis of neoplastic disease may be for the purpose of not only early diagnosis of neoplastic disease but also monitoring of disease progression, therapeutic effect of tumor treatment and response to the treatment, without being limited thereto. The peptide may be labeled for easier identification, detection and quantitation of binding, as described above.

Further, since the peptide of the present invention specifically binds to apoptotic cells, the peptide of the present invention may deliver a drug to apoptotic cells at stroke, myocardial infarction and arteriosclerosis sites, not only at tumor sites. Thus, the present invention provides a pharmaceutical composition for prevention and treatment of stroke comprising the peptide of the present invention and an antistroke agent bound thereto as effective ingredients. Further, the present invention provides a pharmaceutical composition for prevention and treatment of myocardial infarction comprising the peptide of the present invention and an anti-myocardial infarction agent bound thereto as effective ingredients. In addition, the present invention provides a pharmaceutical composition for prevention and treatment of arteriosclerosis comprising the peptide of the present invention and an anti-arteriosclerosis agent bound thereto as effective ingredients.

In addition, the present invention provides a use of the peptide and an antistroke agent bound thereto for the preparation of an agent treating stroke. The present invention provides a method for treating stroke comprising administering the peptide and an antistroke agent bound thereto to a subject in need thereof at an effective dose.

Meanwhile, the present invention provides a use of the peptide and an anti-myocardial infarction agent bound thereto for the preparation of an agent treating myocardial infarction. The present invention provides a method for treating myocardial infarction comprising administering the peptide of the present invention and an anti-myocardial infarction agent bound thereto to a subject in need thereof at an effective dose.

Meanwhile, the present invention provides a use of the peptide of the present invention and an anti-arteriosclerosis agent bound thereto for the preparation of an agent treating arteriosclerosis. The present invention provides a method for treating of arteriosclerosis comprising administering the peptide of the present invention and an anti-arteriosclerosis agent bound thereto to a subject in need thereof at an effective dose.

When used in combination with existing antistroke agent, anti-myocardial infarction agent or anti-arteriosclerosis agent, the peptide of the present invention may selectively deliver the agents to the disease site. Hence, the drug efficiency may be improved and side effects on normal tissues may be significantly reduced.

The anti-myocardial infarction agent, antistroke agent and anti-arteriosclerosis agent agent of the present invention that can be used in combination with the peptide of the present invention may be anyone that is used for treatment thereof, and for example, streptokinase, urokinase, alteplase, angiotensin II inhibitor, aldosterone receptor inhibitor, erythropoietin, NMDA (N-methyl-D-aspartate) receptor inhibitor, Lovastatin, Rapamycin, Celebrex, Ticlopin, Marimastat, Trocade, and etc. may be used. The binding of the peptide of the present invention with the agents may be carried out by the methods known in the art, for example, by covalent bonding, crosslinking, or the like. For this, the peptide of the present invention may be chemically modified insofar as its activity is not lost, if necessary. The amount of the peptide of the present invention included in the composition of the present invention may be different depending on the kind and amount of the agent that the peptide binds to.

Further, since the peptide of the present invention specifically binds to apoptotic cells, it may be useful for imaging and diagnosis of the site of stroke, myocardial infarction and arteriosclerosis. Accordingly, the present invention provides a composition for imaging the site of stroke comprising the peptide of the present invention as an effective ingredient. In addition, the present invention provides a composition for imaging the site of myocardial infarction comprising the peptide as an effective ingredient. Further, the present invention provides a composition for imaging the site of arteriosclerosis comprising the peptide as an effective ingredient.

Meanwhile, the present invention provides a use the peptide of the present invention for imaging a disease site selected from a group consisting of neoplastic disease, stroke, myocardial infarction and arteriosclerosis. The present invention provides a method for imaging a disease site selected from a group consisting of neoplastic disease, stroke, myocardial infarction and arteriosclerosis comprising administering the peptide to a subject in need thereof at an effective dose.

The imaging and diagnosis of disease may be for the purpose of not only early diagnosis of disease but also monitoring of disease progression, therapeutic effect of treatment and response to the treatment, without being limited thereto. The peptide may be labeled for easier identification, detection and quantitation of binding, as described above.

As described, the peptide of the present invention having an amino acid sequence represented by anyone selected from the group consisting of SEQ ID NO: 1 to SEQ ID NO: 12 is capable of specifically binding to apoptotic cells. Accordingly, the peptide of the present invention may be useful for detection of apoptotic cells, as well as detection and imaging of apoptotic cells in tumor tissue, apoptotic myocardial cells in myocardial infarction tissue, apoptotic nerve cells in stroke tissue and arteriosclerosis site, and targeted drug delivery thereto.

EXAMPLES

The examples and experiments will now be described. The following examples and experiments are for illustrative purposes only and not intended to limit the scope of this disclosure.

Example 1

Screening of peptide having binding specificity to the cells of tumor tissue

<1-1> Preparation of phage peptide library

In order to find out peptides specific to various cells constituting a tumor tissue, the inventors of the present invention employed the phage peptide display technique (Smith, *Science*, 228:1315-1317, 1985). Phage peptide display refers to displaying peptides composed of several to dozens of amino acids on the surface of bacteriophage. Since a phage library with as many as $10^9$ peptides can be prepared, the technique is useful in screening a large number of peptides at once and finding out the peptides targeting desired tissue or tumor.

The phage peptide library used in the present invention was prepared as follows. Oligonucleotides coding for $CX_7C$ peptides having cysteine at both ends and 7 random amino acids between them were randomly synthesized. The oligonucleotide synthesis was carried out by Macrogen (Korea). Then, the synthesized oligonucleotides were cloned into the capsid protein gene constituting the surface of T7 415-1 b phage using a T7SELECT® phage cloning kit of Novagen (USA), according to the manufacturer's instructions, thereby preparing phage peptide library. The diversity of the prepared phage peptide library was measured at about $5 \times 10^8$ pfu.

<1-2> Screening of phage peptide library

Tumor tissues and normal tissues neighboring the tumors, which had been obtained from surgical operations for tumor treatment, were finely cut using a knife, and grinded using a tissue homogenizer to prepare a cell suspension. The phage library prepared in Example <1-1> was mixed with the cell suspension obtained from the normal tissue, and they were allowed to react at 4° C. for 2 hours. After completion of the reaction, only the supernatant was taken. After recovering the phages not bound to normal cells, and the titer was amplified using BL21 *E. coli* as host. Subsequently, the cell suspension obtained from the tumor tissue was reacted under the same condition. The phages weakly binding to tumor cells unspecifically were removed by washing with 1 mL of DMEM (Dulbecco's modified Eagle's medium) containing 1% bovine serum albumin (BSA) for 5 minutes at room temperature, for a total of 3 times. Following the washing, magnetic beads on which anti-macrophage antibody (anti-CD14 antibody, Dynal) or anti-endothelial cell antibody (anti-CD31 antibody, Dynal) was attached was reacted with the cell suspension at 4° C. for 30 minutes. Then, the cells adhering to the respective magnetic beads were isolated. The isolated macrophages or endothelial cells were treated with 100 μL of DMEM containing 1% NP-40 at 4° C. for 10 minutes. Then, after adding 900 μL of BL21 *E. coli* culture medium, the phages binding to the cells were detected. The titer was measured for part of the detected phages according to a method known in the art (Phage display, Clackson T and Lowman H B, p. 171, 2004, Oxford University Press, New York). The remaining phages were amplified. This procedure was repeated for a total of 3 times. As a result, the titer of the phages binding to the macrophages and endothelial cells derived from the tumor tissue increased remarkably, therby considering that the screening was successfully performed. The above procedure is schematically shown in FIG. 1.

<1-3> Nucleotide sequencing and amino acid sequencing of phage clone

In order to investigate which peptide was displayed for the phages screened in Example <1-2>, 30 phage clones were randomly selected for each cell, and the nucleotides inserted in the phages were amplified by PCR and sequenced. The 5'-primer was the oligonucleotide AGCGGACCAGATTATCGCTA (SEQ ID NO: 13) and the 3'-primer was the oligonucleotide AACCCCTCAAGACCCGTTTA (SEQ ID NO: 14). PCR was carried out with pre-denaturation of template DNA for 5 minutes at 95° C. ; 35 cycles of 50 seconds at 94° C., 1 minute at 50° C., and 1 minute at 72° C.; and final extention for 6 minutes at 72° C.

The PCR product was sequenced by DNA sequencing company, Bioneer. Based on the resultant nucleotide sequence, the amino acid sequence was deduced. Through analysis of the deduced amino acid sequence using the ClustalW program, the peptides of the representative phage clones most frequently occurring for the macrophages and endothelial cells were obtained, respectively. They represented SEQ ID NO: 1 (ApoPep-1, CQRPPR, screened for the macrophages), SEQ ID NO: 2 (ApoPep-2, CSVAPR, screened for the endothelial cells), SEQ ID NO: 3 (CNRPPR), SEQ ID NO: 4 (CQKPPR), SEQ ID NO: 5 (CQRPPK), SEQ ID NO: 6 (CNKPPR), SEQ ID NO: 7 (CNRPPK), SEQ ID NO: 8 (CQKPPK), SEQ ID NO: 9 (CNKPPK), SEQ ID NO: 10 (CTVAPR), SEQ ID NO: 11 (CSVAPK) and SEQ ID NO: 12 (CTVAPK)

Example 2

Histological evaluation of in vivo tumor targeting by the peptide of the present invention <2-1> Preparation of tumor xenotransplantation model of nude mouse All animal experiments were performed in accordance with the guideline of the Institutional Animal Care and Use Committee. For tumor xenotransplantation, human lung cancer cells (A549, 1×10$^7$ cells) suspended in RMPI-1640 medium was subcutaneously injected at the right upper or lower limb of a 6-week-old male BALB/c nude mouse (Hyochang Science). Then, 3 weeks were given for the tumor to grow to a size of 0.5 to 1 cm. The A549 cell line used in the experiment was cultured in RMPI-1640 medium containing 10% fetal bovine serum (FBS) in which antibiotics (penicillin and streptomycin) were included. Subculturing was performed every 3 or 4 days.

<2-2> Histological analysis of tumor targeting

The peptides used in the present invention were fluorescein-attached form at the N-terminal. They were synthesized according to the standard Fmoc technique and then isolated through HPLC. The peptide synthesis was performed by an expertise company (Peptron).

The peptide of the present invention (ApoPep-1) or a control peptide (amino acid sequence: NSSSVDK), labeled with fluorescein, was injected into the tail vein of a mouse under isoflurane anesthesia, to a final concentration of 50 µM, and 2 hours was given for circulation.

For histological analysis, the mouse was anesthetized and the abdomen was cut open. After sequentially perfusing phosphate-buffered saline (PBS) and 4% paraformaldehyde through the heart, tumor tissues and organs were removed. Each tissue was cryosected and the peptide of the present invention was observed under a fluorescence microscope (Zeiss). Apoptosis in the tumor tissue was confirmed by TUNEL (in vitro terminal deoxynucleotidyl transferase-mediated dUTP nick-end labeling) assay according to the instructions of the manufacturer (Chemicon). Fibrinogen staining was performed by immunohistochemistry using anti-fibrinogen antibody (Abcam) and secondary antibody labeled with Alexa 568, a red fluorescent reagent.

Figure 2:
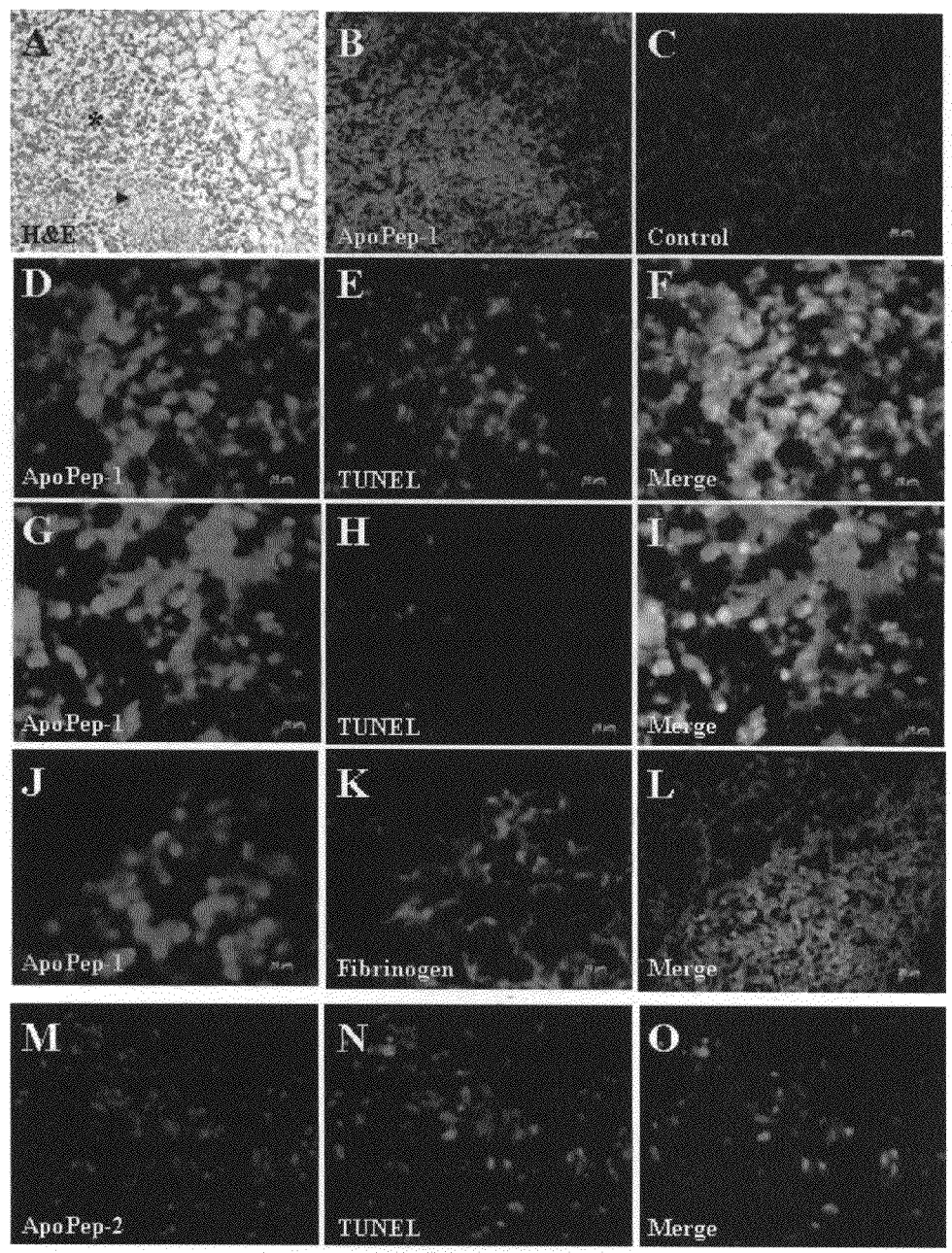
FIG. 2 shows the images obtained as follows. Into the tail vein of a nude mouse to which A549 tumor cells were xenotransplanted under the skin, the peptide of the present invention having an amino acid sequence represented by SEQ ID NO: 1 (ApoPep-1) and being linked with fluorescent label was injected. Images were obtained for H&E staining of the tumor tissue (A), fluorescence of the peptide (B, D, G, J), TUNEL staining (E, H), fibrinogen staining (K) and merge using a computer (F=D+E, I=G+H, L=J+K). C is a fluorescence image of a control peptide. D-F correspond to the location marked by the asterisk in A, and G-I correspond to the location marked by the triangle in A. Also, the same experiment was carried out for the peptide of the present invention having an amino acid sequence represented by SEQ ID NO: 2 (ApoPep-2), and images were obtained fluorescence of the peptide (M), TUNEL staining (N) and merge (O).

As a result, as seen in FIG. 2, tumors were identified by H&E staining (FIG. 2A). The peptide was observed in the tumor tissue when the peptide of the present invention (Apo-Pep-1) was injected (FIG. 2B), but it was hardly observed when the control peptide was injected (FIG. 2C). From the peptide fluorescence (FIG. 2D), TUNEL staining (FIG. 2E) and merge of them (FIG. 2F) at the location marked by the asterisk in FIG. 2A, it was confirmed that the peptide binds to the cells stained by TUNEL, i.e. the apoptotic cells. Further, from the peptide fluorescence (FIG. 2G), TUNEL staining (FIG. 2H) and merge of them (FIG. 2I) at the location marked by the triangle in FIG. 2A, it was confirmed that the peptide also binds to the cells not stained by TUNEL. From the peptide fluorescence (FIG. 2J), fibrinogen staining (FIG. 2K) and merge of them (FIG. 2L) for the location marked by triagle, it was confirmed that the location was coagulation necrotic site.

A similar experiment was performed for the peptide having an amino acid sequence represented by SEQ ID NO: 2 (Apo-Pep-2). From the peptide fluorescence (FIG. 2M), TUNEL staining (FIG. 2N) and merge of them (FIG. 2O), it was confirmed that the peptide binds to the apoptotic cells in the tumor tissue.

Example 3

Binding of the peptide of the present invention to cultured apoptotic cells

<3-1> Microscopic observation of binding of the peptide to apoptotic cells Cells were cultured in chamber slide (Nalgene Nunc) and treated with 50 µM etoposide (Sigma) for a given period of time (A549 and HeLa cells: for 15 hours, H460 cells: 24 hours, L132 cells: 3 hours, RAW cells: 6 hours) to induce apoptosis. The cells were cultured in RMPI-1640 medium (A549 and H460 cells) or DMEM (HeLa, L132 and RAW cells) containing antibiotics (penicillin and streptomycin) and 10% FBS. All the cells were subcultured every 3 or 4 days. The apoptosis-induced apoptotic cells were washed with PBS and blocked with 1% BSA at 37° C. for 30 minutes. Then, the cells were reacted with 10 µM of the peptide labeled with fluorescein, at 4° C. for 1 hour. After washing, the cells were reacted with an annexin V reaction buffer containing Alexa594-labeled annexin V (Molecular Probes), at room temperature for 15 minutes. The cells were washed with PBS and then fixed with 4% paraformaldehyde for 5 minutes. Thereafter, after counterstaining using the nuclear stain 4',6-diamidino-2-phenylindole (DAPI), followed by treatment with a mounting solution (Molecular Probes), images of the cells were obtained under a fluorescence microscope (Zeiss).

Figure 3:
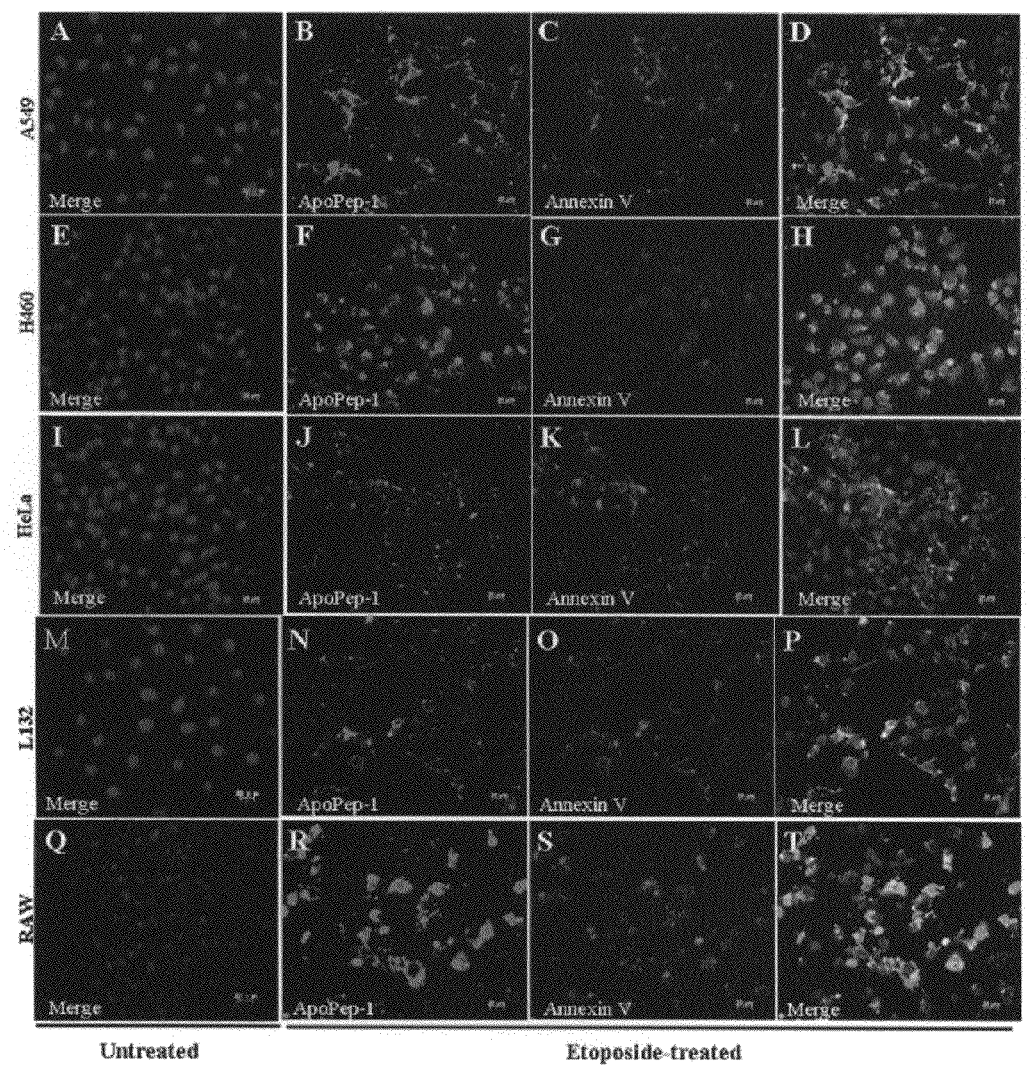
FIG. 3 shows the images obtained as follows. Apoptosis was induced in various cells (A549, H460, HeLa, L132, RAW) by treating with etoposide. Images were obtained for the fluorescence resulting from the binding with the peptide of the present invention (ApoPep-1) (B, F, J, N, R), annexin V staining of the cells (C, G, K, O, S) and merges thereof (D, H, L, P, T). A, E, I, M and Q are merge images of the cells in which apoptosis was not induced, as control group, of binding with the peptide of the present invention (ApoPep-1) or with annexin V.

As a result, as seen in FIG. 3, no labeling was observed when the normal cells, not treated with etoposide, were treated with the peptide of the present invention (ApoPep-1) and annexin V (first column in FIG. 3; A, E, I, M, O). In contrast, labeling was observed in the case of treating with the peptide of the present invention (ApoPep-1) (second column in FIG. 3; B, F, J, N, R) or with annexin V (third column in FIG. 3; C, G, K, O, S), to the etoposide-treated apoptotic cells. Through merge of the images using a computer program, it was confirmed that the bindings for both the peptide of the present invention and annexin V were at the same locations (fourth column in FIG. 3; D, H, L, P, T).

<3-2> Competitive inhibition of binding of the peptide to apoptotic cells by annexin V treatment In order to further investigate the binding properties of the peptide of the present invention (ApoPep-1) to apoptotic cells, competitive inhibition by annexin V was measured. To this end, first, apoptotic A549 cells were pre-treated with annexin V, not labeled with fluorescence, at concentrations of 0, 200 and 1000 µM. Then, after reacting the cells with fluorescence-labeled annexin V under the same condition as described in Example <3-1>, the binding of the cells was observed under a fluorescence microscope.

As a result, as seen in FIG. 4A-C, the fluorescence decreased significantly when annexin V, not labeled with fluorescence, was pre-treated at high concentration due to competitive inhibition of the binding with fluorescence-labeled annexin V.

Further, apoptotic A549 cells were pre-treated with annexin V, not labeled with fluorescence, at a concentration of 1000 µM. Then, after reacting the cells with fluorescence-labeled peptide under the same condition as described in Example <3-1>, the binding of the cells was observed under a fluorescence microscope.

Figure 4:
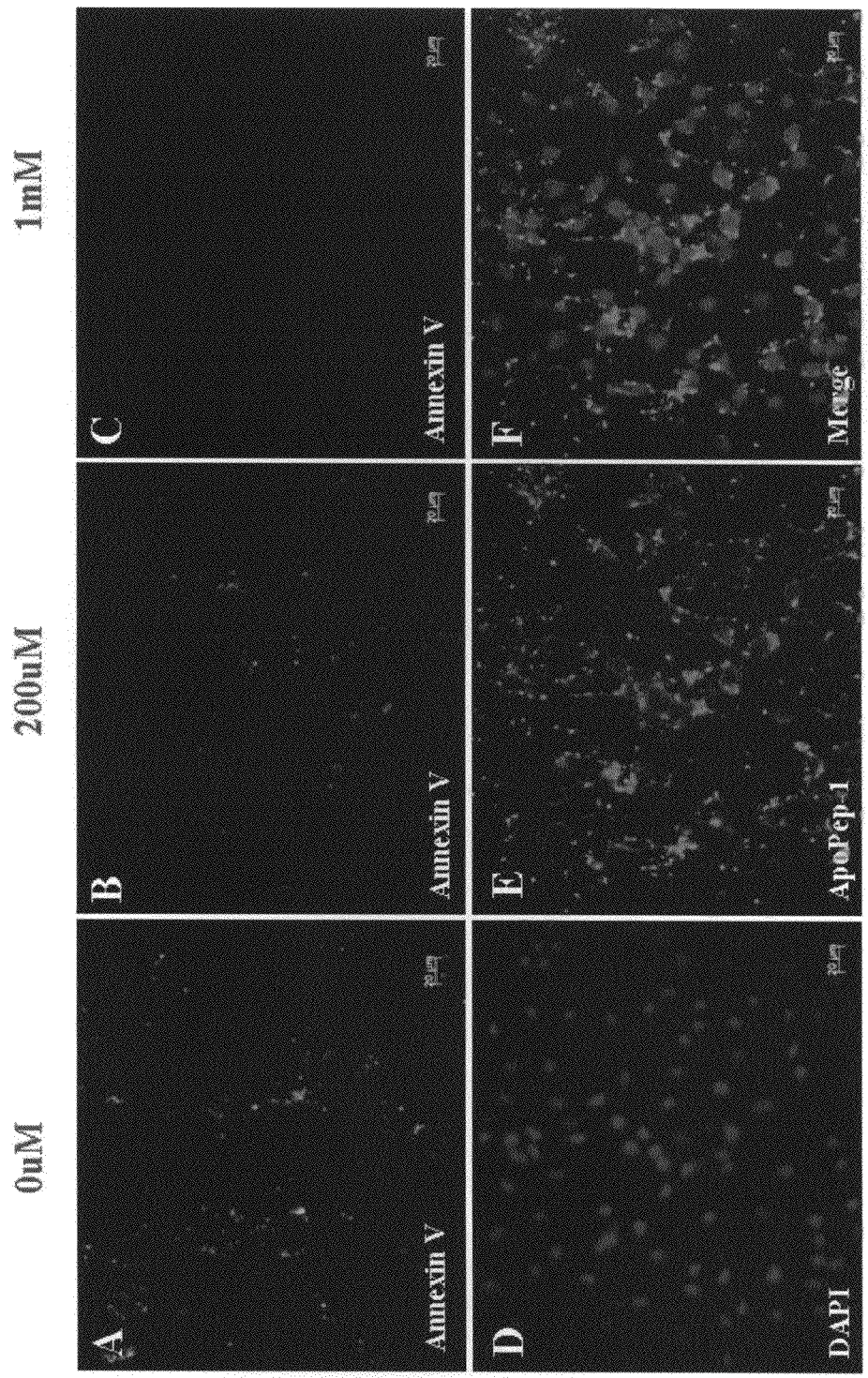
FIG. 4 shows the images obtained as follows. Apoptosis was induced in A549 tumor cell by treating with etoposide. Imaged were obtained by staining with red fluorescence-labeled annexin V after pre-treating with annexin V without a fluorescence label at concentrations of 0 pM (A), 200 pM (B) and 1000 pM (C). Further, after pre-treating with annexin V at 1000 μM, images were obtained for binding with the peptide of the present invention (ApoPep-1) (E), nuclear staining (D) and a merge thereof (F).

As a result, as seen in FIG. 4, D-F, the binding of the peptide of the present invention (ApoPep-1) was not inhibited by the treatment with annexin V at high concentration.

<3-3> Confirmation of binding of the peptide of the present invention to apoptotic cells through FACS analysis As another way of confirming the binding of the peptide of the present invention to apoptotic cells, apoptotic cells were treated with the peptide of the present invention, labeled with fluorescein, and the binding was confirmed through FACS analysis. First, apoptosis was induced by treating A549 cells with 50 μM etoposide for 6 to 15 hours. The apoptotic cells or normal cells were reacted with ApoPep-1 (5 μM), ApoPep-2 (10 μM) or a control peptide at the same concentrations, labeled with fluorescein, at 4° C. for 1 hour. Further, the cells were reacted with fluorescein-labeled annexin V at room temperature for 15 minutes. After staining the cells with propodium iodide(PI) simultaneously, followed by washing with PBS, FACS analysis was performed using a FACS instrument (Becton Dickinson).

Figure 5:
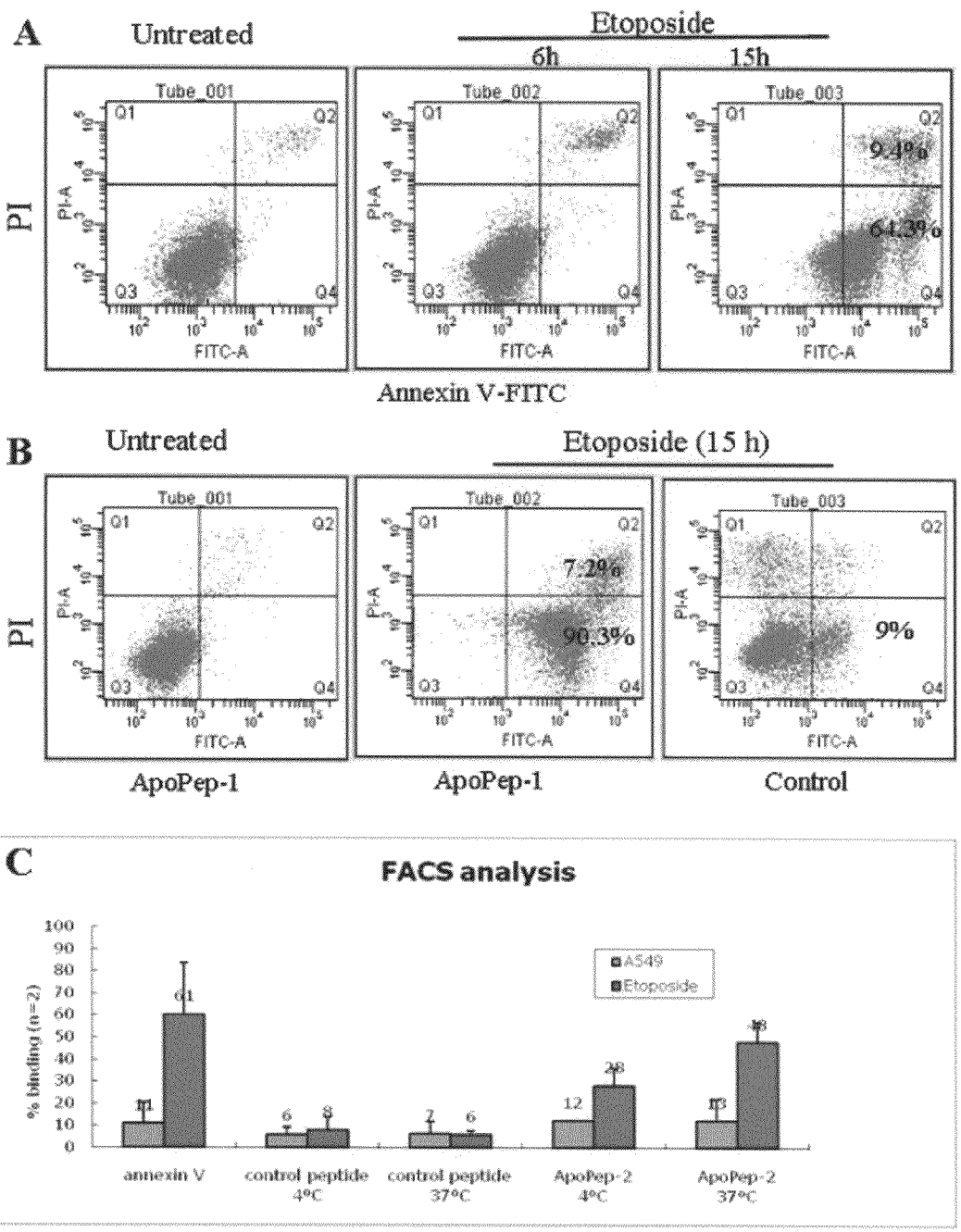
FIG. 5 shows FACS analysis result of binding of A549 tumor cells, treated with or without etoposide, with annexin V (A), and the peptide of the present invention (ApoPep-1) or a control peptide (Control) (B). The abscissa represents the degree of binding to annexin V or the peptide, and the ordinate represents the degree of propidium iodide (PI) staining. C shows FACS analysis result of binding of the cells with the peptide of the present invention (ApoPep-2) or the control peptide at 4° C. and 37° C. (A549: etoposide non-treated group; Etoposide: etoposide treated group).

As a result, as seen in FIG. 5, when the etoposide-treated apoptotic A549 cells were stained with annexin V and PI, the percentage of the cells stained only by annexin V (fraction Q4, early stage of apoptosis) and the percentage of the cells stained by both annexin V and PI (fraction Q2, later stage of apoptosis) were 64.3% and 9.4%, respectively, at 15 hours, which were higher than at 6 hours (FIG. 5A). Further, when the cells that had been treated with etoposide for 15 hours were treated with ApoPep-1, 90.3% and 7.2% of the cells at the early stage and later stage of apoptosis, respectively, were bound to the peptide (FIG. 5B). In contrast, when the apoptotic cells were treated with the control peptide or when the normal cells were treated with the peptide of the present invention (ApoPep-1), the binding was almost nonexistent.

Further, when the apoptotic A549 cells that had been treated with etoposide for 20 hours were treated with ApoPep-2 peptide, at 4° C. or 37° C. for 1 hour, the peptide bound better to the apoptotic cells than to the normal cells (FIG. 5C).

Example 4

Targeting of apoptotic cells in tumor by the peptide of the present invention and imaging thereof <4-1> Targeting of apoptotic cells in tumor by the peptide and imaging thereof Nude mice in which tumor was xenotransplanted using A549 cells were prepared as in Example <2-1>. The mice were grouped into a doxorubicin (Sigma) treated group (+Dox) and untreated group (−Dox). The treated group was treated with doxorubicin (10 mg/kg) 3 times, with an interval of 48 hours, a week prior to injection of the peptide. At the tail vein of each mouse, the peptide of the present invention or a control peptide, labeled with fluorescein, was injected at a final concentration of 50 μM, under isoflurane anesthesia. Following the injection, in vivo fluorescence images were obtained every hour, from 1 hour to 6 hours after the injection, using an Optix exPlore instrument (GE Healthcare). The images were standardized using the software provided with the instrument.

Further, when the tumor grew considerably (1 cm or larger in diameter), the peptide of the present invention was injected at the same concentration as above, without doxorubicin treatment, and in vivo fluorescence images were obtained at every given time using an IVIS fluorescence imaging system (Chemipro).

Figure 6:
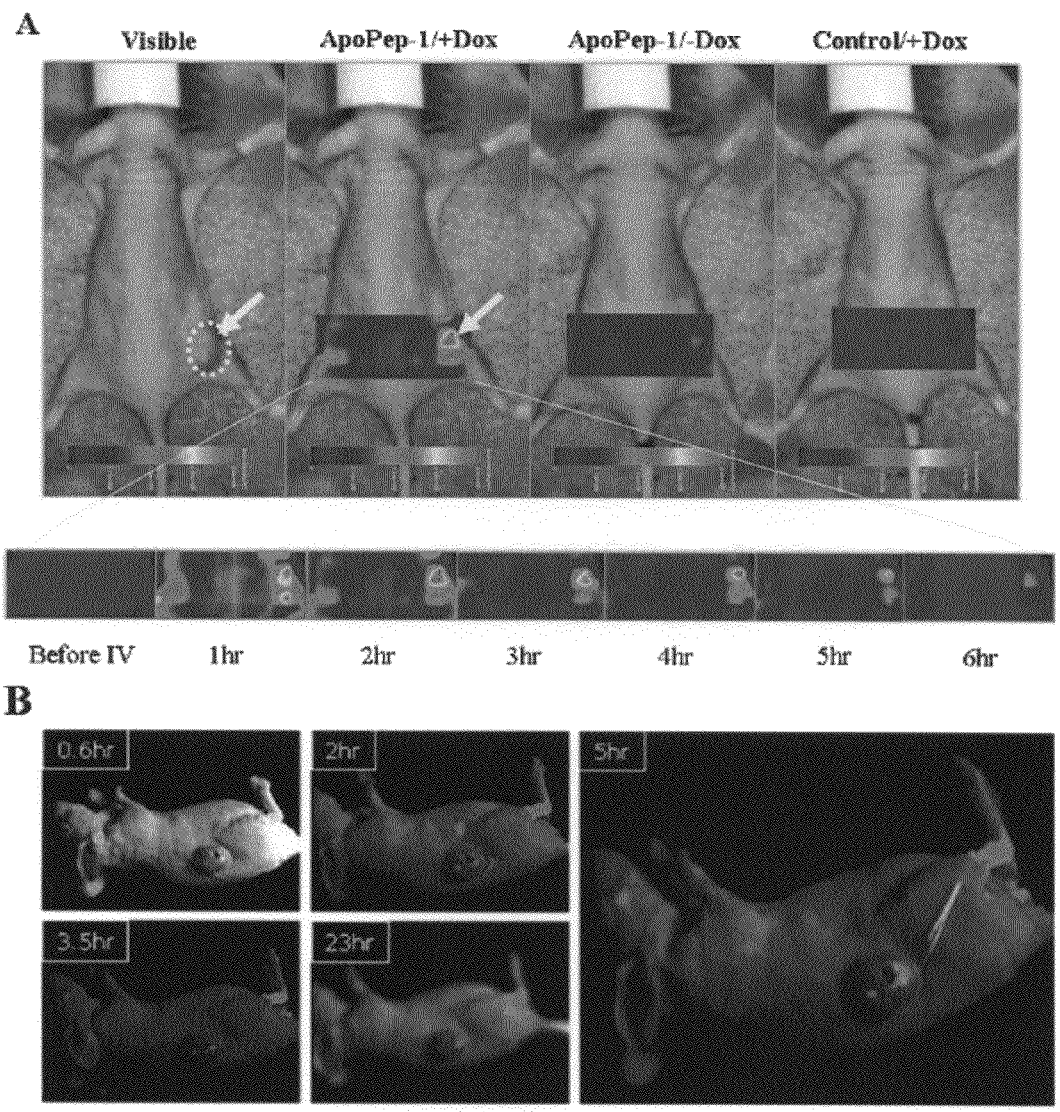
FIG. 6 shows the images obtained as follows. A nude mouse to which a tumor was xenotransplanted was treated with or without doxorubicin. 24 hours later, the peptide having an amino sequence represented by SEQ ID NO: 1 (ApoPep-1) (A) and the peptide having an amino sequence represented by SEQ ID NO: 2 (ApoPep-2) (B), which were labeled with fluorescence, were injected into blood. The peptides were traced in vivo based on fluorescence.

As a result, as seen in FIG. 6A, when ApoPep-1 was injected to the doxorubicin treated group, the fluorescence signal from the tumor tissue by fluorescein was the most strongly detected at 2 hours, and the signal was detected until at 5 hours. In contrast, when the peptide of the present invention was injected to the doxorubicin untreated group or when the control peptide was injected to the doxorubicin treated group, the fluorescence signal was weakly detected or almost nonexistent.

Further, as seen in FIG. 6B, when ApoPep-2 was injected to a mouse with a large tumor (1 cm or larger in diameter), the fluorescence from the tumor was detected from 2 hours. A strong fluorescence signal was detected at 5 hours. This implies that in the large-sized tumor, apoptosis occurred significantly in the tumor tissue in spite of the absence of treatment of an agent.

<4-2> Radionuclide imaging of targeting of apoptotic cells in tumor by the peptide Nude mice in which tumor was xenotransplanted using H460 cells were prepared as in Example <2-1>. The mice were grouped into a doxorubicin (Sigma) treated group and untreated group. The treated group was treated with doxorubicin (10 mg/kg) 3 times, with an interval of 48 hours, a week prior to injection of the peptide. The peptide of the present invention (ApoPep-1), labeled with the radioactive isotope 124I, was injected through the tail vein of each mouse under isoflurane anesthesia (treated group: 91 μCi; untreated group: 93 μCi). Further, $^{18}$F-labeled FDG, which is frequently used for PET, was injected to the doxorubicin treated group and untreated group, at 300 μCi and 304 μCi, respectively. Radionuclide images were obtained using a micro PET instrument (Concorde MicroSystems) 5 hours after the injection of [$^{124}$I]ApoPep-1 and 1 hour after the injection of [$^{18}$F]FDG.

Figure 7:
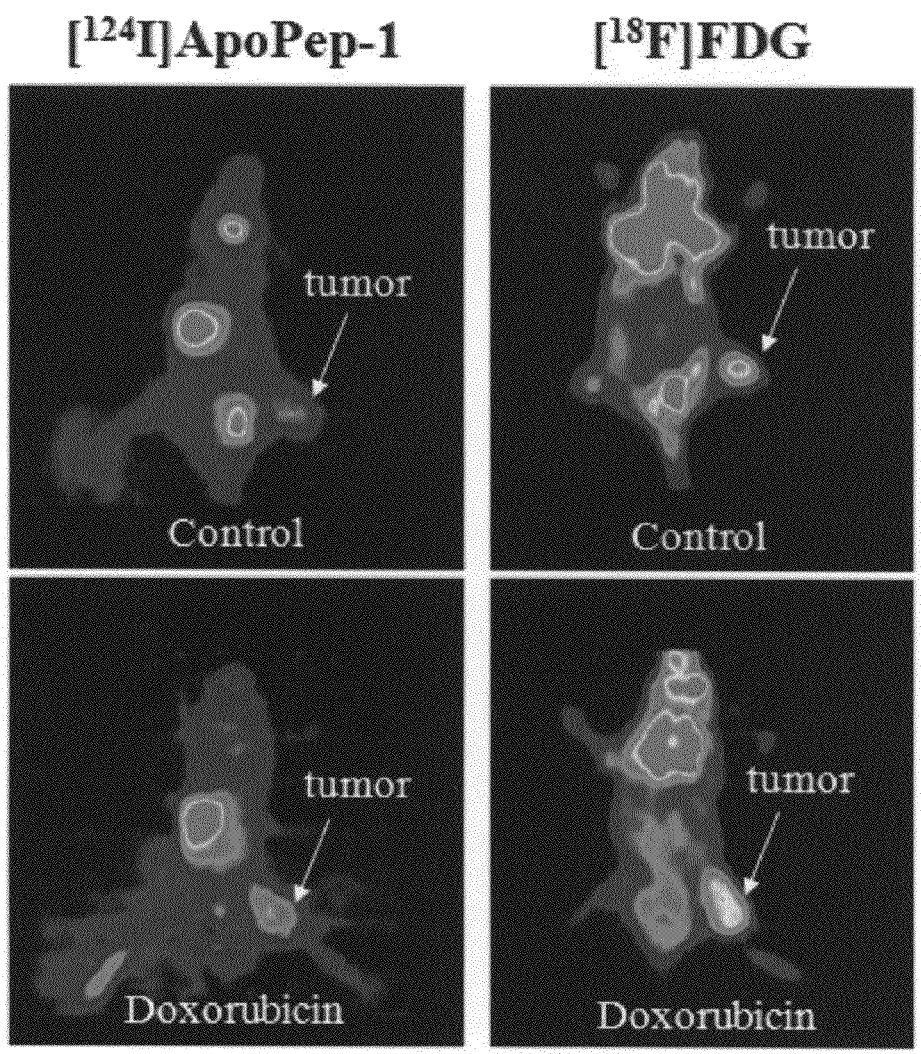
FIG. 7 shows the images obtained as follows. A nude mouse to which a tumor was xenotransplanted was treated with doxorubicin. 24 hours later, $^{18}F$-labeled FDG and the peptide having an amino sequence represented by SEQ ID NO: 1 (ApoPep-1), which was labeled with $^{124}$I-labeled, were injected into blood. They were traced in vivo using a micro PET.

As a result, as seen in FIG. 7, when [$^{124}$I]ApoPep-1 was injected, a much stronger signal was observed at the tumor site in the doxorubicin treated group as compared with the untreated group. In contrast, for [$^{18}$F]FDG, a weaker signal was observed in the doxorubicin treated group as compared with the untreated group. This implies that the peptide of the present invention is capable of recognizing and monitoring the apoptosis of tumor cells induced by the anticancer drug treatment.

Example 5

Molecular imaging of arteriosclerosis using the peptide of the present invention An arteriosclerotic animal model was established by feeding mice, in which low-density lipoprotein (LDL) receptor was deficient (LdIr(−/−)) genetically, with a high-cholesterol diet for 8 weeks. At the tail vein of the arteriosclerotic mouse and normal mouse, the peptide having an amino sequence represented by SEQ ID NO: 1 (ApoPep-1) or a control peptide, labeled with Cy7.5 NIR fluorescence, was injected at a final concentration of 50 μM, under isoflurane anesthesia. Two hours later, with the mouse anesthetized, in vivo images of the NIR fluorescence were obtained using an Optix exPlore instrument. Following the in vivo imaging, NIR fluorescence was measured in vitro after isolating the aorta.

Figure 8:
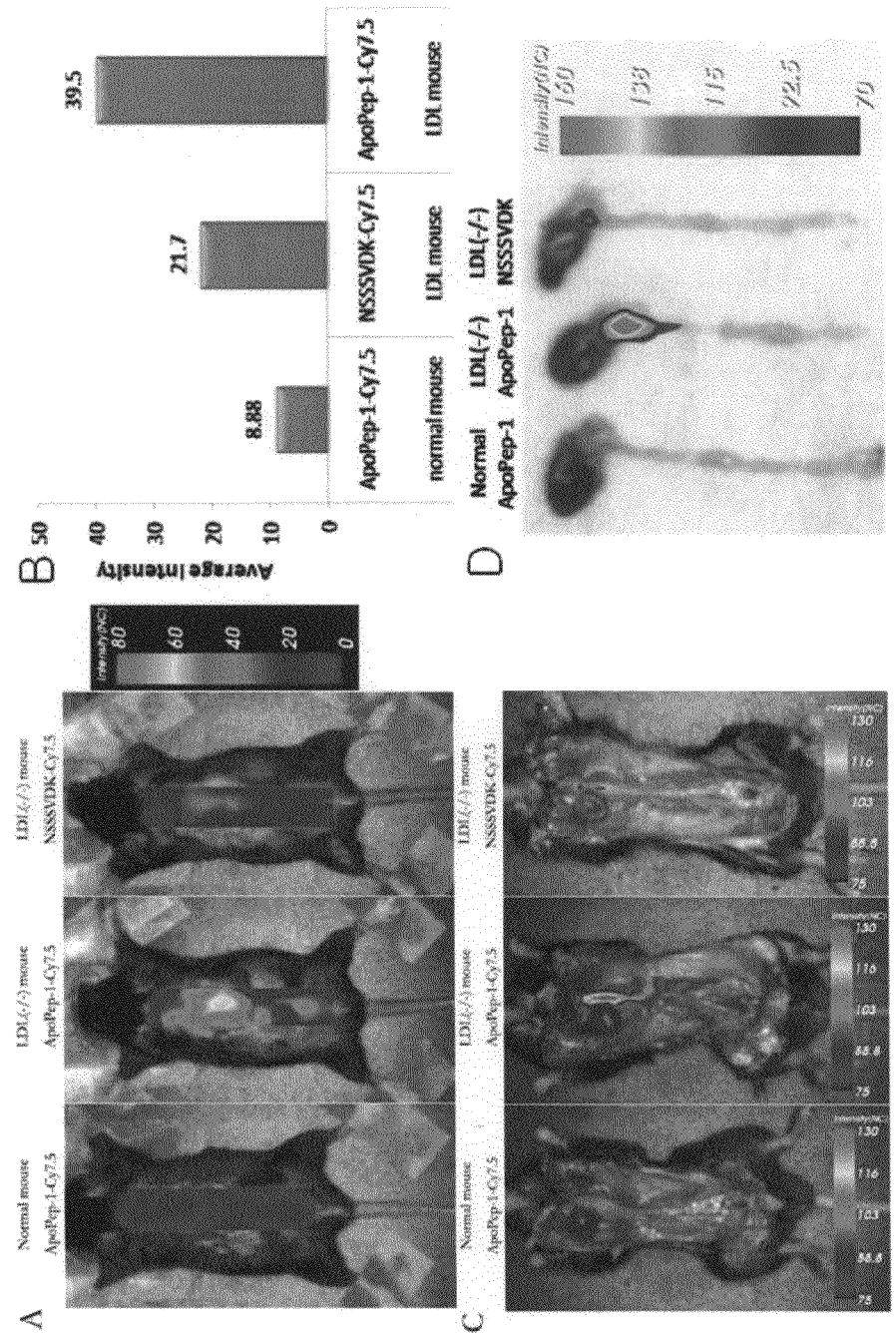
FIG. 8 shows the images obtained as follows. To an arteriosclerosis model mouse in which low-density lipoprotein (LDL) receptor was deleted genetically (LdIr(-/-)) and a normal mouse, the peptide having an amino sequence represented by SEQ ID NO: 1 (ApoPep-1), which was labeled with Cy7.5 near infrared (NIR) fluorescence, was intravenously injected. One hour later, NIR images were obtained from the back (A) or after exposing the aorta by cutting the abdomen open (C). B shows the intensity of NIR in A. D shows NIR images of the aorta isolated from each mouse (ApoPep-1-Cy7.5: Cy7.5-labeled ApoPep-1; NSSSVDK-Cy7.5: Cy7.5-labeled control peptide).

As a result, when the images were obtained from the back, a stronger NIR fluorescence was observed in the arteriosclerotic mouse to which ApoPep-1 was injected than the mouse to which the control peptide was injected. Fluorescence was almost nonexistent in the normal mouse, despite the injection of ApoPep-1 (FIG. 8A). The intensity of the fluorescence due to the peptide of the present invention was about two times that of the control peptide (FIG. 8B). When the images were obtained after exposing the aorta by cutting the abdomen open, the NIR fluorescence was much stronger in the arteriosclerotic mouse to which ApoPep-1 was injected as compared with that to which the control peptide was injected (FIG. 8C). A similar result was obtained when the fluorescence was measured in vitro after isolating the aorta (FIG. 8D).

Example 6

Molecular imaging of stroke using the peptide of the present invention

A stroke model was established by occluding the left middle cerebral artery of a rat for 2 hours, followed by reperfusion. Two hours after the reperfusion, the peptide having an amino sequence represented by SEQ ID NO: 1 (ApoPep-1) and a control peptide, labeled with Cy7.5 NIR fluorescence, was intravenously injected at a final concentration of 50 μM to the stroke rat and a normal rat through the tail vein, under isoflurane anesthesia. One and three hours after the intravenous injection, NIR images of the head portion were obtained. Further, NIR fluorescence images of the brains of the rats of the 3 hour group were obtained.

As a result, NIR fluorescence was observed at 1 hour at the head portion of the stroke rat to which the peptide of the present invention (ApoPep-1) was injected, and a very strong fluorescence was observed at 3 hours. In contrast, fluorescence was almost nonexistent in the stroke rat to which the control peptide (NSSSVDK) was injected or in the normal rat to which ApoPep-1 was injected (FIG. 9A). A similar result was obtained when the brains were isolated from the rats and fluorescence was observed in vitro. Especially, fluorescence was observed at the left hemisphere of the stroke rat, since the left middle cerebral artery had been occluded (FIG. 9B).

Example 7

Molecular imaging of myocardial ischemia using the peptide of the present invention

A myocardial ischemia model was established by occluding the coronary artery of a rat, followed by reperfusion (ischemia/reperfusion model). For the operation, a rat was anesthetized by intra-abdominally injecting 10 mg of phenobarbital and, followed by endobronchial intubation, a ventilator was connected. Thereafter, the thorax was cut open to expose the heart. The left anterior descending coronary artery was occluded for 30 minutes using a suture and, then, the blood was allowed to circulate. For a control group (Sham), the same operation was performed, except for the occlusion. Two hours after the reperfusion, the peptide having an amino sequence represented by SEQ ID NO: 1 (ApoPep-1), labeled with Cy7.5 NIR fluorescence, was intravenously injected to the rats of the myocardial ischemia group and the control group. Two hours after the peptide injection, NIR images of the heart portion were obtained. Then, NIR images were obtained after isolating the heart.

Figure 10:
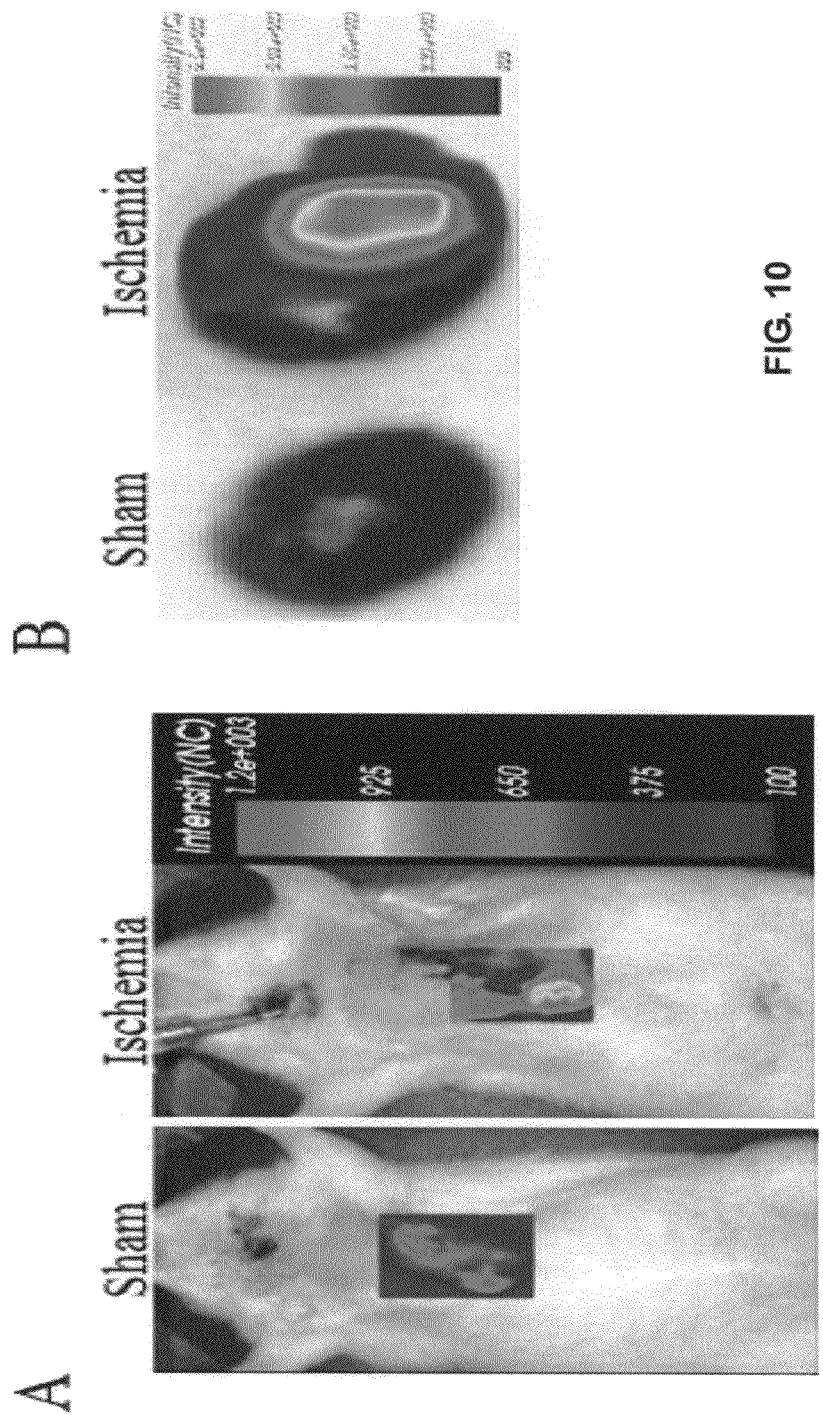
FIG. 10 shows the images obtained as follows. To a myocardial ischemic rat and a control rat (Sham), the peptide having an amino sequence represented by SEQ ID NO: 1 (ApoPep-1), which was labeled with Cy7.5 NIR fluorescence, was intravenously injected. Two hours later, NIR images of the heart portion were obtained (A). Then, NIR images of the hearts of the rats were obtained (B).

As a result, a much stronger NIR fluorescence was observed in the myocardial ischemic rat than in the control group rat (FIG. 10A). A similar result was obtained when the fluorescence was measured in vitro after isolating the heart (FIG. 10B).

As can be seen the foregoing, the peptide of the present invention may be capable of specific binding with the apoptotic cells. Accordingly, the peptide of the present invention may be useful for detection of apoptotic cells in tumor, for detection of apoptotic cells in myocardial infarction, stroke or arteriosclerosis site, for imaging of diagnosis or target drug delivery and so on.

---

The invention claimed is:

1. An isolated polypeptide consisting of SEQ ID NO: 1 or 3 and specifically binding apoptotic cells.

2. A method for detecting apoptotic cells comprising the steps of:
   (a) mixing the polypeptide of claim 1 with a sample;
   (b) removing unbound or unspecifically bound polypeptide; and
   (c) detecting the binding and the location of the polypeptide.

3. The method of claim 2, wherein the polypeptide is labeled with a labeling agent selected from the group consisting of coloring enzyme, radioactive isotope, chromophore, scintillating material, fluorescer, super paramagnetic particles and ultrasuper paramagnetic particles.

4. A method for drug delivery comprising administering the polypeptide of claim 1 and a drug bound thereto to a subject in need thereof at an effective dose.

5. The method of claim 4, wherein the method is specific to the disease selected from the group consisting of neoplastic disease, stroke, myocardial infarction and arteriosclerosis.

6. The method of claim 4, wherein the neoplastic disease is selected from the group consisting of colon cancer, lung cancer, stomach cancer, esophageal cancer, pancreatic cancer, gallbladder cancer, renal cancer, bladder cancer, prostate cancer, testicular cancer, cervical cancer, endometrial cancer, choriocarcinoma, ovarian cancer, breast cancer, thyroid cancer, brain cancer, head and neck cancer, malignant melanoma, skin cancer, liver cancer, leukemia, lymphoma, multiple myeloma, chronic myelogenous leukemia, neuroblastoma and aplastic anemia.

7. The method of claim 4, wherein the drug is selected from the group consisting of paclitaxel, doxorubicin, vincristine, daunorubicin, vinblastine, actinomycin-D, docetaxel, etoposide, teniposide, bisantrene, homoharringtonine, Gleevec (STI-571), cisplatin, 5-fluorouracil, Adriamycin, methotrexate, busulfan, chlorambucil, cyclophosphamide, melphalan, nitrogen mustard, nitrosourea, streptokinase, urokinase, alteplase, angiotensin II inhibitor, aldosterone receptor inhibitor, erythropoietin, NMDA (N-methyl-D-aspartate) receptor inhibitor lovastatin, rapamycin, Celebrex, Ticlopin, Marimastat and Trocade.

8. A pharmaceutical composition for treating neoplastic disease comprising i) an isolated polypeptide consisting of SEQ ID NO: 1 or 3 and specifically binding apoptotic cells; and ii) an antitumor agent bound thereto as effective ingredients, wherein the antitumor agent is selected from the group consisting of paclitaxel, doxorubicin, vincristine, daunorubicin, vinblastine, actinomycin-D, docetaxel, etoposide, teniposide, bisantrene, homoharringtonine, Gleevec (STI-571), cisplatin, 5-fluorouracil, adriamycin, methotrexate, busulfan, chlorambucil, cyclophosphamide, melphalan, nitrogen mustard and nitrosourea; wherein the neoplastic disease is selected from the group consisting of colon cancer, lung cancer, stomach cancer, esophageal cancer, pancreatic cancer, gallbladder cancer, renal cancer, bladder cancer, prostate cancer, testicular cancer, cervical cancer, endometrial cancer, choriocarcinoma, ovarian cancer, breast cancer, thyroid cancer, brain cancer, head and neck cancer, malignant melanoma, skin cancer, liver cancer, leukemia, lymphoma, multiple myeloma, chronic myelogenous leukemia, neuroblastoma and aplastic anemia.

9. A pharmaceutical composition for treating stroke comprising i) an isolated polypeptide consisting of SEQ ID NO: 1 or 3 and specifically binding apoptotic cells; and ii) an anti-stroke agent bound thereto as effective ingredients, wherein the anti-stroke agent is selected from the group consisting of streptokinase, urokinase and alteplase.

10. A pharmaceutical composition for treating myocardial infarction comprising i) an isolated polypeptide consisting of SEQ ID NO: 1 or 3 and specifically binding apoptotic cells; and ii) an anti-myocardial infarction agent bound thereto as effective ingredients, wherein the anti-myocardial infarction agent is selected from the group consisting of streptokinase, urokinase, alteplase, angiotensin II inhibitor, aldosterone receptor inhibitor, erythropoietin and N-methyl-D-aspartate receptor inhibitor.

11. A pharmaceutical composition for treating arteriosclerosis comprising i) an isolated polypeptide consisting of SEQ ID NO: 1 or 3 and specifically binding apoptotic cells; and ii) an anti-arteriosclerosis agent bound thereto as effective ingredients, wherein the anti-arteriosclerosis agent is selected from the group consisting of lovastatin, rapamycin, Celebrex, Ticlogin, Marimastat, and Trocade.

12. A method for treating neoplastic disease comprising administering the polypeptide of claim 1 and an antitumor agent bound thereto to a subject in need thereof at an effective dose; wherein the antitumor agent is selected from the group consisting of paclitaxel, doxorubicin, vincristine, daunorubicin, vinblastine, actinomycin-D, docetaxel, etoposide, teniposide, bisantrene, homoharringtonine, Gleevec (STI-571), cisplatin, 5-fluorouracil, adriamycin, methotrexate, busulfan, chlorambucil, cyclophosphamide, melphalan, nitrogen mustard and nitrosourea; and wherein the neoplastic disease is selected from the group consisting of colon cancer, lung cancer, stomach cancer, esophageal cancer, pancreatic cancer, gallbladder cancer, renal cancer, bladder cancer, prostate cancer, testicular cancer, cervical cancer, endometrial cancer, choriocarcinoma, ovarian cancer, breast cancer, thyroid cancer, brain cancer, head and neck cancer, malignant melanoma, skin cancer, liver cancer, leukemia, lymphoma, multiple myeloma, chronic myelogenous leukemia, neuroblastoma and aplastic anemia.

13. A method for treating stroke comprising administering the polypeptide of claim 1 and an antistroke agent bound thereto to a subject in need thereof at an effective dose; wherein the anti-stroke agent is selected from the group consisting of streptokinase, urokinase, and alteplase.

14. A method for treating myocardial infarction comprising administering the polypeptide of claim 1 and an anti-myocardial infarction agent bound thereto to a subject in need thereof at an effective dose; wherein the anti-myocardial infarction agent is selected from the group consisting of streptokinase, urokinase, alteplase, angiotensin II inhibitor, aldosterone receptor inhibitor, erythropoietin and N-methyl-D-aspartate receptor inhibitor.

15. A method for treating arteriosclerosis comprising administering the polypeptide of claim 1 and an anti-arteriosclerosis agent bound thereto to a subject in need thereof at an effective dose; wherein the anti-arteriosclerosis agent is selected from the group consisting of lovastatin, rapamycin, Celebrex, Ticlogin, Marimastat and Trocade.

16. A method for imaging a site of disease selected from the group consisting of neoplastic disease, stroke, myocardial infarction and arteriosclerosis comprising administering the polypeptide of claim 1 labeled with a labeling agent, to a subject in need thereof at an effective dose.

17. The method of claim 16, wherein the labeling agent is selected from the group consisting of coloring enzyme, radioactive isotope, chromophore, scintillating material, fluorescer, super paramagnetic particles and ultrasuper paramagnetic particles.

* * * * *

SEQUENCE LISTING

```
<160> NUMBER OF SEQ ID NOS: 14

<210> SEQ ID NO 1
<211> LENGTH: 6
<212> TYPE: PRT
<213> ORGANISM: Artificial Sequence
<220> FEATURE:
<223> OTHER INFORMATION: Peptide 1 for targeting apoptotic cells

<400> SEQUENCE: 1

Cys Gln Arg Pro Pro Arg
  1               5

<210> SEQ ID NO 2
<211> LENGTH: 6
<212> TYPE: PRT
<213> ORGANISM: Artificial Sequence
<220> FEATURE:
<223> OTHER INFORMATION: Peptide 2 for targeting apoptotic cells

<400> SEQUENCE: 2

Cys Ser Val Ala Pro Arg
  1               5

<210> SEQ ID NO 3
<211> LENGTH: 6
<212> TYPE: PRT
<213> ORGANISM: Artificial Sequence
<220> FEATURE:
<223> OTHER INFORMATION: peptide 3 for targeting apoptotic cells
```

-continued

```
<400> SEQUENCE: 3

Cys Asn Arg Pro Pro Arg
  1               5

<210> SEQ ID NO 4
<211> LENGTH: 6
<212> TYPE: PRT
<213> ORGANISM: Artificial Sequence
<220> FEATURE:
<223> OTHER INFORMATION: peptide 4 for targeting apoptotic cells

<400> SEQUENCE: 4

Cys Gln Lys Pro Pro Arg
  1               5

<210> SEQ ID NO 5
<211> LENGTH: 6
<212> TYPE: PRT
<213> ORGANISM: Artificial Sequence
<220> FEATURE:
<223> OTHER INFORMATION: peptide 5 for targeting apoptotic cells

<400> SEQUENCE: 5

Cys Gln Arg Pro Pro Lys
  1               5

<210> SEQ ID NO 6
<211> LENGTH: 6
<212> TYPE: PRT
<213> ORGANISM: Artificial Sequence
<220> FEATURE:
<223> OTHER INFORMATION: peptide 6 for targeting apoptotic cells

<400> SEQUENCE: 6

Cys Asn Lys Pro Pro Arg
  1               5

<210> SEQ ID NO 7
<211> LENGTH: 6
<212> TYPE: PRT
<213> ORGANISM: Artificial Sequence
<220> FEATURE:
<223> OTHER INFORMATION: peptide 7 for targeting apoptotic cells

<400> SEQUENCE: 7

Cys Asn Arg Pro Pro Lys
  1               5

<210> SEQ ID NO 8
<211> LENGTH: 6
<212> TYPE: PRT
<213> ORGANISM: Artificial Sequence
<220> FEATURE:
<223> OTHER INFORMATION: peptide 8 for targeting apoptotic cells

<400> SEQUENCE: 8

Cys Gln Lys Pro Pro Lys
  1               5

<210> SEQ ID NO 9
<211> LENGTH: 6
<212> TYPE: PRT
<213> ORGANISM: Artificial Sequence
<220> FEATURE:
<223> OTHER INFORMATION: peptide 9 for targeting apoptotic cells

<400> SEQUENCE: 9
```

```
Cys Asn Lys Pro Pro Lys
  1               5

<210> SEQ ID NO 10
<211> LENGTH: 6
<212> TYPE: PRT
<213> ORGANISM: Artificial Sequence
<220> FEATURE:
<223> OTHER INFORMATION: peptide 10 for targeting apoptotic cells

<400> SEQUENCE: 10

Cys Thr Val Ala Pro Arg
  1               5

<210> SEQ ID NO 11
<211> LENGTH: 6
<212> TYPE: PRT
<213> ORGANISM: Artificial Sequence
<220> FEATURE:
<223> OTHER INFORMATION: peptide 11 for targeting apoptotic cells

<400> SEQUENCE: 11

Cys Ser Val Ala Pro Lys
  1               5

<210> SEQ ID NO 12
<211> LENGTH: 6
<212> TYPE: PRT
<213> ORGANISM: Artificial Sequence
<220> FEATURE:
<223> OTHER INFORMATION: peptide 12 for targeting apoptotic cells

<400> SEQUENCE: 12

Cys Thr Val Ala Pro Lys
  1               5

<210> SEQ ID NO 13
<211> LENGTH: 20
<212> TYPE: DNA
<213> ORGANISM: Artificial Sequence
<220> FEATURE:
<223> OTHER INFORMATION: forward primer

<400> SEQUENCE: 13
agcggaccag attatcgcta                                           20

<210> SEQ ID NO 14
<211> LENGTH: 20
<212> TYPE: DNA
<213> ORGANISM: Artificial Sequence
<220> FEATURE:
<223> OTHER INFORMATION: reverse primer

<400> SEQUENCE: 14
aacccctcaa gacccgttta                                           20
```